US009585933B2

(12) United States Patent
Pagano

(10) Patent No.: US 9,585,933 B2
(45) Date of Patent: Mar. 7, 2017

(54) THERAPEUTIC USE OF PEPTIDE INHIBITORS OF NADPH OXIDASE; AEROSOLIZATION AS A DELIVERY MECHANISM

(71) Applicant: University of Pittsburgh—Of the Commonwealth System of Higher Education, Pittsburgh, PA (US)

(72) Inventor: Patrick J. Pagano, Sewickley, PA (US)

(73) Assignee: University of Pennsylvania—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/608,655

(22) Filed: Jan. 29, 2015

(65) Prior Publication Data

US 2015/0297670 A1 Oct. 22, 2015

Related U.S. Application Data

(63) Continuation of application No. 13/473,758, filed on May 17, 2012, now Pat. No. 8,962,570.

(60) Provisional application No. 61/486,837, filed on May 17, 2011.

(51) Int. Cl.

| | |
|---|---|
| ***A61K 38/10*** | (2006.01) |
| ***A61K 38/08*** | (2006.01) |
| ***A61P 9/00*** | (2006.01) |
| ***A61P 11/00*** | (2006.01) |

(52) U.S. Cl.

CPC .............. *A61K 38/10* (2013.01); *A61K 38/08* (2013.01)

(58) Field of Classification Search

CPC ................................ A61K 38/08; A61K 38/10

See application file for complete search history.

(56) References Cited

U.S. PATENT DOCUMENTS

2010/0172971 A1 7/2010 McCarty et al.
2011/0152172 A1 6/2011 Anderson et al.

FOREIGN PATENT DOCUMENTS

WO 0117533 A1 3/2001

OTHER PUBLICATIONS

DeLeo et al, Characterization of peptide diffusion into electropermeabilized neutrophils, Journal of Immunological Methods, 1996, 198, pp. 35-49.*

Csanyi, G. et al., Nox2 B-loop Peptide, Nox 2ds, Specifically Inhibits Nox2 Oxidase, Free Radical Biology & Medicine, Sep. 15, 2011, pp. 1116-1125, vol. 51, No. 6.

Csanyi, G. et al., Nox2ds is a Selective Therapeutic Inhibitor of Nox2 NADPH oxidase, Poster Presented at Gordon International Conference, Jun. 2010.

Griffith, B. et al., NOX Enzymes and Pulmonary Disease, Antioxidants & Redox Signaling, 2009, pp. 2505-2516, vol. 11, No. 10.

Judkins, C.P. et al., Direct evidence of a role for Nox2 in superoxide production, reduced nitric oxide bioavailability, and early atherosclerotic plaque formation in ApoE mice, American Journal of Physiology—Heart and Circulatory Physiology, 2010, pp. H24-H32, vol. 298.

Judkins, C.P. et al., NADPH oxidases in vascular biology and disease, Proceedings of the Australian Physiological Society, 2008, 39/132P.

Lambeth, J.D. et al., NOX enzymes as novel targets for drug development, Seminars in Immunopathology, 2008, pp. 339-363, vol. 30.

Madamanchi, N.R. et al., NADPH oxidases and atherosclerosis: unraveling the details, American Journal of Physiology—Heart and Circulatory Physiology, 2010, pp. H1-H2, vol. 298.

National Center for Biotechnology Information, Cytochrome b-245, beta polypeptide (*Homo sapiens*), Gene ID: 1536, 8 pages, Jun. 18, 2012.

National Center for Biotechnology Information, Cytochrome b-245, beta polypeptide, mRNA (*Homo sapiens*), GenBank Accession No. NM_000397, 6 pages, Jun. 18, 2012.

National Center for Biotechnology Information, Cytochrome b-245 heavy chain (*Homo sapiens*), GenBank Accession No. NP_000388, 4 pages, Jun. 18, 2012.

National Center for Biotechnology Information, Cytochrome b-245 heavy chain (*Mus musculus*), GenBank Accession No. NP_031833, 3 pages, Jun. 18, 2012.

Online Mendelian Inheritance in Man, OMIM, Cytochrome b-245, beta subunit, MIM No. 300481, Mar. 2, 2004, 24 pages, Johns Hopkins University, Baltimore, MD.

Online Mendelian Inheritance in Man, OMIM, Granulomatous disease, chronic, x-linked, cgd, MIM No. 306400, Jun. 4, 1986, 25 pages, Johns Hopkins University, Baltimore, MD.

Park, L. et al., Nox2-derived radicals contribute to neurovascular and behavioral dysfunction in mice overexpressing the amyloid precursor protein, Proceedings of the National Academy of Sciences of the USA, Jan. 29, 2008, pp. 1347-1352, vol. 105, No. 4.

Peterson, G., Recent Advances in the Design and Synthesis of Peptidomimetics, Evans Group Literature Seminar, Apr. 13, 2001, 40 pages.

Price, M.O. et al., Creation of a genetic system for analysis of the phagocyte respiratory burst: high-level reconstitution of the NADPH oxidase in a nonhematopoietic system, Blood, Apr. 15, 2002, pp. 2653-2661, vol. 99, No. 8.

(Continued)

*Primary Examiner* — Julie Ha
*Assistant Examiner* — Li Ni Komatsu
(74) *Attorney, Agent, or Firm* — The Webb Law Firm

(57) ABSTRACT

A method is provided for treatment of a condition mediated by Nox2 in a patient. The method comprises administering to the patient by inhalation a polypeptide as described herein, able to inhibit superoxide production by Nox2. Conditions treatable in this manner include, without limitation, one or more of: right ventricular hypertrophy; pulmonary hypertension; acute lung injury; obstructive sleep apnea; ischemia/reperfusion injury in the lung; pulmonary fibrosis; an obstructive lung disorder such as Chronic Obstructive Pulmonary Disease (COPD), asthma, cystic fibrosis and emphysema; and atherosclerosis.

20 Claims, 11 Drawing Sheets

(56) References Cited

OTHER PUBLICATIONS

Rey, F.E. et al., Novel Competitive Inhibitor of NAD(P)H Oxidase Assembly Attenuates Vascular O2 and Systolic Blood Pressure in Mice, Circulation Research, 2001, pp. 408-414.

Sciarra, J.J. et al., Chapter 50: Aerosols, in Remington: The Science and Practice of Pharmacy, 21st Edition, Eds. Paul Beringer et al., 2006, pp. 1000-1017, Lippincott, Williams & Wilkins, Philadelphia, PA.

Sebbage, V., Cell-penetrating peptides and their therapeutic applications, Bioscience Horizons, Mar. 2009, pp. 64-72, vol. 2, No. 1.

Vagner, J. et al., Peptidomimetics, a synthetic tool of drug discovery, Current Opinion in Chemical Biology, 2008, pp. 292-296, vol. 12, No. 3.

Veronese, F.M. et al, PEGylation, successful approach to drug delivery, Drug Discovery Today, Nov. 2005, pp. 1451-1458, vol. 10, No. 21.

Zhao, L. et al., Sildenafil Inhibits Hypoxia-Induced Pulmonary Hypertension, Circulation, 2001, pp. 424-428, vol. 104.

Zekry et al., A Role for NOX NADPH Oxidases in Alzheimer's Disease and Other Types of Dementia?, IUBMB Life, 2003, 55, pp. 307-313.

Cave et al., NADPH Oxidases in Cardiovascular Health and Disease, Antioxidants & Redox Signaling, 2006, 8, pp. 691-728.

Lung Disease Alphabetical Listing, from American Lung Association, pp. 1-2, accessed, Apr. 3, 2013.

Liu et al., Hypoxic pulmonary hypertension: role of superoxide and NADPH oxidase (gp9lphox), Am J Physiol Lung Cell Mol Physiol, 2006, 290, pp. L2-L10.

Patton et al., The Lungs as a Portal of Entry for Systemic Drug Delivery, Proc Am Thorac Soc, 2004, 1, pp. 338-344.

* cited by examiner (SEQ ID NO 1)

```
  1 mgnwavnegl sifvilvwlg lnvflfvwyy rvydippkff ytrkllgsal alarapaacl
 61 nfncmlillp vcrnllsflr gssaccstrv rrqldrnltf hkmvawmial hsaihtiahl
121 fnvewcvnar vnnsdpysva lselgdrqne sylnfarkri knpegglyla vtllagitgv
181 vitlclilii tsstktirrs yfevfwythh lfviffigla ihgaerivrg qtaeslavhn
241 itvceqkise wgkikecpip qfagnppmtw kwivgpmfly lcerlvrfwr sqqkvvitkv
301 vthpfktiel qmkkkgfkme vgqyifvkcp kvsklewhpf tltsapeedf fsihirivgd
361 wteglfnacg cdkqefqdaw klpkiavdgp fgtasedvfs yevvmlvgag igvtpfasil
421 ksvwykycnn atnlklkkiy fywlcrdtha fewfadllql lesqmqernn agflsyniyl
481 tgwdesqanh favhhdeekd vitglkqktl ygrpnwdnef ktiasqhpnt rigvflcgpe
541 alaetlskqs isnsesgprg vhfifnkenf
```

*Fig. 1A*

(SEQ ID NO: 2)

```
   1 attggaagaa gaagcatagt atagaagaaa ggcaaacaca acacattcaa cctctgccac
  61 catggggaac tgggctgtga atgaggggct ctccattttt gtcattctgg tttggctggg
 121 gttgaacgtc ttcctctttg tctggtatta ccgggtttat gatattccac ctaagttctt
 181 ttacacaaga aaacttcttg ggtcagcact ggcactggcc agggcccctg cagcctgcct
 241 gaatttcaac tgcatgctga ttctcttgcc agtctgtcga aatctgctgt ccttcctcag
 301 gggttccagt gcgtgctgct caacaagagt tcgaagacaa ctggacagga atctcacctt
 361 tcataaaatg gtggcatgga tgattgcact tcactctgcg attcacacca ttgcacatct
 421 atttaatgtg gaatggtgtg tgaatgcccg agtcaataat tctgatcctt attcagtagc
 481 actctctgaa cttggagaca ggcaaaatga aagttatctc aattttgctc gaaagagaat
 541 aaagaaccct gaaggaggcc tgtacctggc tgtgaccctg ttggcaggca tcactggagt
 601 tgtcatcacg ctgtgcctca tattaattat cacttcctcc accaaaacca tccggaggtc
 661 ttactttgaa gtcttttggt acacacatca tctctttgtg atcttcttca ttggccttgc
 721 catccatgga gctgaacgaa ttgtacgtgg gcagaccgca gagagtttgg ctgtgcataa
 781 tataacagtt tgtgaacaaa aaatctcaga atggggaaaa ataaaggaat gcccaatccc
 841 tcagtttgct ggaaaccctc ctatgacttg gaaatggata gtgggtccca tgtttctgta
 901 tctctgtgag aggttggtgc ggttttggcg atctcaacag aaggtggtca tcaccaaggt
 961 ggtcactcac cctttcaaaa ccatcgagct acagatgaag aagaaggggt tcaaaatgga
1021 agtgggacaa tacatttttg tcaagtgccc aaaggtgtcc aagctggagt ggcacccttt
1081 tacactgaca tccgcccctg aggaagactt ctttagtatc catatccgca tcgttgggga
1141 ctggacagag gggctgttca atgcttgtgg ctgtgataag caggagtttc aagatgcgtg
1201 gaaactacct aagatagcgg ttgatgggcc ctttggcact gccagtgaag atgtgttcag
1261 ctatgaggtg gtgatgttag tgggagcagg gattggggtc acacccttcg catccattct
1321 caagtcagtc tggtacaaat attgcaataa cgccaccaat ctgaagctca aaaagatcta
1381 cttctactgg ctgtgccggg acacacatgc ctttgagtgg tttgcagatc tgctgcaact
1441 gctggagagc cagatgcagg aaaggaacaa tgccggcttc ctcagctaca acatctacct
1501 cactggctgg gatgagtctc aggccaatca ctttgctgtg caccatgatg aggagaaaga
1561 tgtgatcaca ggcctgaaac aaaagacttt gtatggacgg cccaactggg ataatgaatt
1621 caagacaatt gcaagtcaac accctaatac cagaatagga gttttcctct gtggacctga
1681 agccttggct gaaaccctga gtaaacaaag catctccaac tctgagtctg gccctcgggg
1741 agtgcatttc attttcaaca aggaaaactt ctaacttgtc tcttccatga ggaaataaat
1801 gtgggttgtg ctgccaaatg ctcaaataat gctaattgat aatataaata ccccctgctt
1861 aaaaatggac aaaaagaaac tataatgtaa tggttttccc ttaaaggaat gtcaaagatt
1921 gtttgatagt gataagttac atttatgtgg agctctatgg ttttgagagc acttttacaa
1981 acattatttc atttttttcc tctcagtaat gtcagtggaa gttagggaaa agattcttgg
2041 actcaatttt agaatcaaaa gggaaaggat caaaaggttc agtaacttcc ctaagattat
2101 gaaactgtga ccagatctag cccatcttac tccaggtttg atactctttc cacaatactg
2161 agctgcctca gaatcctcaa aatcagtttt tatattcccc aaaagaagaa ggaaaccaag
2221 gagtagctat atatttctac tttgtgtcat ttttgccatc attattatca tactgaagga
2281 aattttccag atcattagga cataatacat gttgagagtg tctcaacact tattagtgac
2341 agtattgaca tctgagcata ctccagttta ctaatacagc agggtaactg ggccagatgt
2401 tctttctaca gaagaatatt ggattgattg gagttaatgt aatactcatc atttaccact
2461 gtgcttggca gagagcggat actcaagtaa gttttgttaa atgaatgaat gaatttagaa
2521 ccacacaatg ccaagataga attaatttaa agccttaaac aaaatttatc taaagaaata
2581 acttctatta ctgtcataga ccaaaggaat ctgattctcc ctagggtcaa gaacaggcta
2641 aggatactaa ccaataggat tgcctgaagg gttctgcaca ttcttatttg aagcatgaaa
2701 aaagagggtt ggaggtggag aattaacctc ctgccatgac tctggctcat ctagtcctgc
```

*Fig. 1B-1*

```
2761 tccttgtgct ataaaataaa tgcagactaa tttcctgccc aaagtggtct tctccagcta
```

```
2821 gcccttatga atattgaact taggaattgt gacaaatatg tatctgatat ggtcatttgt
2881 tttaaataac acccacccct tattttccgt aaatacacac acaaaatgga tcgcatctgt
2941 gtgactaatg gtttatttgt attatatcat catcatcatc ctaaaattaa caacccagaa
3001 acaaaaatct ctatacagag atcaaattca cactcaatag tatgttctga atatatgttc
3061 aagagagagt ctctaaatca ctgttagtgt ggccaagagc agggttttct ttttgttctt
3121 agaactgctc ccatttctgg gaactaaaac cagttttatt tgccccaccc cttggagcca
3181 caaatgttta gaactcttca acttcggtaa tgaggaagaa ggagaaagag ctgggggaag
3241 ggcagaagac tggtttagga ggaaaaggaa ataaggagaa aagagaatgg gagagtgaga
3301 gaaaataaaa aaggcaaaag ggagagagag gggaaggggg tctcatattg gtcattccct
3361 gccccagatt tcttaaagtt tgatatgtat agaatataat tgaaggaggt atacacatat
3421 tgatgttgtt ttgattatct atggtattga atcttttaaa atctggtcac aaattttgat
3481 gctgaggggg attattcaag ggactaggat gaactaaata agaactcagt tgttctttgt
3541 catactacta ttcctttcgt ctcccagaat cctcagggca ctgagggtag gtctgacaaa
3601 taaggcctgc tgtgcgaata tagcctttct gaaatgtacc aggatggttt ctgcttagag
3661 acacttaggt ccagcctgtt cacactgcac ctcaggtatc aattcatcta ttcaacagat
3721 atttattgtg ttattactat gagtcaggct ctgtttattg tttcaattct ttacaccaaa
3781 gtatgaactg gagagggtac ctcagttata aggagtctga gaatattggc cctttctaac
3841 ctatgtgcat aattaaaacc agcttcattt gttgctccga gagtgtttct ccaaggtttt
3901 ctatcttcaa aaccaactaa gttatgaaag tagagagatc tgccctgtgt tatccagtta
3961 tgagataaaa aatgaatata agagtgcttg tcattataaa agtttccttt tttattctct
4021 caagccacca gctgccagcc accagcagcc agctgccagc ctagcttttt tttttttttt
4081 ttttttttag cacttagtat ttagcattta ttaacaggta ctctaagaat gatgaagcat
4141 tgtttttaat cttaagacta tgaaggtttt tcttagttct tctgcttttg caattgtgtt
4201 tgtgaaattt gaatacttgc aggctttgta tgtgaataat tctagcgggg gacctgggag
4261 ataattccta cggggaattc ttaaaactgt gctcaactat taaaatgaat gagctttcaa
4321 aaaaaaaaaa aaaaaaaaaa aaaaaaaaaa aaa
```

*Fig. 1B-2*

(SEQ ID NO: 3)

```
  1 mgnwavnegl sifvilvwlg lnvflfinyy kvyddgpkyn ytrkllgsal alarapaacl
 61 nfncmlillp vcrnlisflr gssaccstri rrqldrnltf hkmvawmial htaihtiahl
121 fnvewcvnar vgisdrysia lsdigdnene eylnfareki knpegglyva vtrlagitgi
181 vitlclilii tsstktirrs yfevfwythh lfviffigla ihgaerivrg qtaesleehn
241 ldicadkiee wgkikecpvp kfagnppmtw kwivgpmfly lcerlvrfwr sqqkvvitkv
301 vthpfktiel qmkkkgfkme vgqyifvkcp kvsklewhpf tltsapeedf fsihirivgd
361 wteglfnacg cdkqefqdaw klpkiavdgp fgtasedvfs yevvmlvgag igvtpfasil
421 ksvwykycdn atslklkkiy fywlcrdtha fewfadllql letqmqernn anflsyniyl
481 tgwdesqanh favhhdeekd vitglkqktl ygrpnwdnef ktiasehpnt tigvflcgpe
541 alaetlskqs isnsesgprg vhfifnkenf
```

*Fig. 1C*

SEQUENCE LISTING

```
<160> NUMBER OF SEQ ID NOS: 13

<210> SEQ ID NO 1
<211> LENGTH: 570
<212> TYPE: PRT
<213> ORGANISM: Homo sapiens

<400> SEQUENCE: 1
```

-continued

```
Met Gly Asn Trp Ala Val Asn Glu Gly Leu Ser Ile Phe Val Ile Leu
1               5                   10                  15

Val Trp Leu Gly Leu Asn Val Phe Leu Phe Val Trp Tyr Tyr Arg Val
            20                  25                  30

Tyr Asp Ile Pro Pro Lys Phe Phe Tyr Thr Arg Lys Leu Leu Gly Ser
        35                  40                  45

Ala Leu Ala Leu Ala Arg Ala Pro Ala Ala Cys Leu Asn Phe Asn Cys
    50                  55                  60

Met Leu Ile Leu Leu Pro Val Cys Arg Asn Leu Leu Ser Phe Leu Arg
65                  70                  75                  80

Gly Ser Ser Ala Cys Cys Ser Thr Arg Val Arg Arg Gln Leu Asp Arg
                85                  90                  95

Asn Leu Thr Phe His Lys Met Val Ala Trp Met Ile Ala Leu His Ser
            100                 105                 110

Ala Ile His Thr Ile Ala His Leu Phe Asn Val Glu Trp Cys Val Asn
        115                 120                 125

Ala Arg Val Asn Asn Ser Asp Pro Tyr Ser Val Ala Leu Ser Glu Leu
    130                 135                 140

Gly Asp Arg Gln Asn Glu Ser Tyr Leu Asn Phe Ala Arg Lys Arg Ile
145                 150                 155                 160

Lys Asn Pro Glu Gly Gly Leu Tyr Leu Ala Val Thr Leu Leu Ala Gly
                165                 170                 175

Ile Thr Gly Val Val Ile Thr Leu Cys Leu Ile Leu Ile Ile Thr Ser
            180                 185                 190

Ser Thr Lys Thr Ile Arg Arg Ser Tyr Phe Glu Val Phe Trp Tyr Thr
        195                 200                 205

His His Leu Phe Val Ile Phe Phe Ile Gly Leu Ala Ile His Gly Ala
    210                 215                 220

Glu Arg Ile Val Arg Gly Gln Thr Ala Glu Ser Leu Ala Val His Asn
225                 230                 235                 240

Ile Thr Val Cys Glu Gln Lys Ile Ser Glu Trp Gly Lys Ile Lys Glu
                245                 250                 255

Cys Pro Ile Pro Gln Phe Ala Gly Asn Pro Pro Met Thr Trp Lys Trp
            260                 265                 270

Ile Val Gly Pro Met Phe Leu Tyr Leu Cys Glu Arg Leu Val Arg Phe
        275                 280                 285

Trp Arg Ser Gln Gln Lys Val Val Ile Thr Lys Val Val Thr His Pro
    290                 295                 300

Phe Lys Thr Ile Glu Leu Gln Met Lys Lys Lys Gly Phe Lys Met Glu
305                 310                 315                 320

Val Gly Gln Tyr Ile Phe Val Lys Cys Pro Lys Val Ser Lys Leu Glu
                325                 330                 335

Trp His Pro Phe Thr Leu Thr Ser Ala Pro Glu Glu Asp Phe Phe Ser
            340                 345                 350

Ile His Ile Arg Ile Val Gly Asp Trp Thr Glu Gly Leu Phe Asn Ala
        355                 360                 365

Cys Gly Cys Asp Lys Gln Glu Phe Gln Asp Ala Trp Lys Leu Pro Lys
    370                 375                 380

Ile Ala Val Asp Gly Pro Phe Gly Thr Ala Ser Glu Asp Val Phe Ser
385                 390                 395                 400

Tyr Glu Val Val Met Leu Val Gly Ala Gly Ile Gly Val Thr Pro Phe
                405                 410                 415

Ala Ser Ile Leu Lys Ser Val Trp Tyr Lys Tyr Cys Asn Asn Ala Thr
```

-continued

```
            420                 425                 430

Asn Leu Lys Leu Lys Lys Ile Tyr Phe Tyr Trp Leu Cys Arg Asp Thr
        435                 440                 445

His Ala Phe Glu Trp Phe Ala Asp Leu Leu Gln Leu Leu Glu Ser Gln
    450                 455                 460

Met Gln Glu Arg Asn Asn Ala Gly Phe Leu Ser Tyr Asn Ile Tyr Leu
465                 470                 475                 480

Thr Gly Trp Asp Glu Ser Gln Ala Asn His Phe Ala Val His His Asp
                485                 490                 495

Glu Glu Lys Asp Val Ile Thr Gly Leu Lys Gln Lys Thr Leu Tyr Gly
            500                 505                 510

Arg Pro Asn Trp Asp Asn Glu Phe Lys Thr Ile Ala Ser Gln His Pro
        515                 520                 525

Asn Thr Arg Ile Gly Val Phe Leu Cys Gly Pro Glu Ala Leu Ala Glu
    530                 535                 540

Thr Leu Ser Lys Gln Ser Ile Ser Asn Ser Glu Ser Gly Pro Arg Gly
545                 550                 555                 560

Val His Phe Ile Phe Asn Lys Glu Asn Phe
                565                 570
```

<210> SEQ ID NO 2
<211> LENGTH: 4353
<212> TYPE: DNA
<213> ORGANISM: Homo sapiens

<400> SEQUENCE: 2

```
attggaagaa gaagcatagt atagaagaaa ggcaaacaca acacattcaa cctctgccac     60
catggggaac tgggctgtga atgaggggct ctccattttt gtcattctgg tttggctggg    120
gttgaacgtc ttcctctttg tctggtatta ccgggtttat gatattccac ctaagttctt    180
ttacacaaga aaacttcttg ggtcagcact ggcactggcc agggcccctg cagcctgcct    240
gaatttcaac tgcatgctga ttctcttgcc agtctgtcga aatctgctgt ccttcctcag    300
gggttccagt gcgtgctgct caacaagagt tcgaagacaa ctggacagga atctcacctt    360
tcataaaatg gtggcatgga tgattgcact tcactctgcg attcacacca ttgcacatct    420
atttaatgtg gaatggtgtg tgaatgcccg agtcaataat tctgatcctt attcagtagc    480
actctctgaa cttggagaca ggcaaaatga aagttatctc aattttgctc gaaagagaat    540
aaagaaccct gaaggaggcc tgtacctggc tgtgaccctg ttggcaggca tcactggagt    600
tgtcatcacg ctgtgcctca tattaattat cacttcctcc accaaaacca tccggaggtc    660
ttactttgaa gtcttttggt acacacatca tctctttgtg atcttcttca ttggccttgc    720
catccatgga gctgaacgaa ttgtacgtgg gcagaccgca gagagtttgg ctgtgcataa    780
tataacagtt tgtgaacaaa aaatctcaga atggggaaaa ataaaggaat gcccaatccc    840
tcagtttgct ggaaaccctc ctatgacttg gaaatggata gtgggtccca tgtttctgta    900
tctctgtgag aggttggtgc ggttttggcg atctcaacag aaggtggtca tcaccaaggt    960
ggtcactcac cctttcaaaa ccatcgagct acagatgaag aagaaggggt tcaaaatgga   1020
agtgggacaa tacatttttg tcaagtgccc aaaggtgtcc aagctggagt ggcacccttt   1080
tacactgaca tccgcccctg aggaagactt ctttagtatc catatccgca tcgttgggga   1140
ctggacagag gggctgttca atgcttgtgg ctgtgataag caggagtttc aagatgcgtg   1200
gaaactacct aagatagcgg ttgatgggcc ctttggcact gccagtgaag atgtgttcag   1260
```

-continued ctatgaggtg gtgatgttag tgggagcagg gattggggtc acacccttcg catccattct 1320
caagtcagtc tggtacaaat attgcaataa cgccaccaat ctgaagctca aaaagatcta 1380
cttctactgg ctgtgccggg acacacatgc ctttgagtgg tttgcagatc tgctgcaact 1440
gctggagagc cagatgcagg aaaggaacaa tgccggcttc ctcagctaca acatctacct 1500
cactggctgg gatgagtctc aggccaatca ctttgctgtg caccatgatg aggagaaaga 1560
tgtgatcaca ggcctgaaac aaaagacttt gtatggacgg cccaactggg ataatgaatt 1620
caagacaatt gcaagtcaac accctaatac cagaatagga gttttcctct gtggacctga 1680
agccttggct gaaaccctga gtaaacaaag catctccaac tctgagtctg gccctcgggg 1740
agtgcatttc attttcaaca aggaaaactt ctaacttgtc tcttccatga ggaaataaat 1800
gtgggttgtg ctgccaaatg ctcaaataat gctaattgat aatataaata ccccctgctt 1860
aaaaatggac aaaaagaaac tataatgtaa tggttttccc ttaaaggaat gtcaaagatt 1920
gtttgatagt gataagttac atttatgtgg agctctatgg ttttgagagc acttttacaa 1980
acattatttc atttttttcc tctcagtaat gtcagtggaa gttagggaaa agattcttgg 2040
actcaatttt agaatcaaaa gggaaaggat caaaaggttc agtaacttcc ctaagattat 2100
gaaactgtga ccagatctag cccatcttac tccaggtttg atactctttc cacaatactg 2160
agctgcctca gaatcctcaa aatcagtttt tatattcccc aaaagaagaa ggaaaccaag 2220
gagtagctat atatttctac tttgtgtcat ttttgccatc attattatca tactgaagga 2280
aattttccag atcattagga cataatacat gttgagagtg tctcaacact tattagtgac 2340
agtattgaca tctgagcata ctccagttta ctaatacagc agggtaactg ggccagatgt 2400
tctttctaca gaagaatatt ggattgattg gagttaatgt aatactcatc atttaccact 2460
gtgcttggca gagagcggat actcaagtaa gttttgttaa atgaatgaat gaatttagaa 2520
ccacacaatg ccaagataga attaatttaa agccttaaac aaaatttatc taaagaaata 2580
acttctatta ctgtcataga ccaaaggaat ctgattctcc ctagggtcaa gaacaggcta 2640
aggatactaa ccaataggat tgcctgaagg gttctgcaca ttcttatttg aagcatgaaa 2700
aaagagggtt ggaggtggag aattaacctc ctgccatgac tctggctcat ctagtcctgc 2760
tccttgtgct ataaaataaa tgcagactaa tttcctgccc aaagtggtct tctccagcta 2820
gcccttatga atattgaact taggaattgt gacaaatatg tatctgatat ggtcatttgt 2880
tttaaataac acccacccct tattttccgt aaatacacac acaaaatgga tcgcatctgt 2940
gtgactaatg gtttatttgt attatatcat catcatcatc ctaaaattaa caacccagaa 3000
acaaaaatct ctatacagag atcaaattca cactcaatag tatgttctga atatatgttc 3060
aagagagagt ctctaaatca ctgttagtgt ggccaagagc agggttttct ttttgttctt 3120
agaactgctc ccatttctgg gaactaaaac cagttttatt tgccccaccc cttggagcca 3180
caaatgttta gaactcttca acttcggtaa tgaggaagaa ggagaaagag ctgggggaag 3240
ggcagaagac tggtttagga ggaaaaggaa ataaggagaa aagagaatgg gagagtgaga 3300
gaaaataaaa aaggcaaaag ggagagagag gggaaggggg tctcatattg gtcattccct 3360
gccccagatt tcttaaagtt tgatatgtat agaatataat tgaaggaggt atacacatat 3420
tgatgttgtt ttgattatct atggtattga atcttttaaa atctggtcac aaattttgat 3480
gctgaggggg attattcaag ggactaggat gaactaaata agaactcagt tgttctttgt 3540
catactacta ttcctttcgt ctcccagaat cctcagggca ctgagggtag gtctgacaaa 3600
taaggcctgc tgtgcgaata tagcctttct gaaatgtacc aggatggttt ctgcttagag 3660
acacttaggt ccagcctgtt cacactgcac ctcaggtatc aattcatcta ttcaacagat 3720
atttattgtg ttattactat gagtcaggct ctgtttattg tttcaattct ttacaccaaa 3780
gtatgaactg gagagggtac ctcagttata aggagtctga gaatattggc cctttctaac 3840
ctatgtgcat aattaaaacc agcttcattt gttgctccga gagtgtttct ccaaggtttt 3900
ctatcttcaa aaccaactaa gttatgaaag tagagagatc tgccctgtgt tatccagtta 3960
tgagataaaa aatgaatata agagtgcttg tcattataaa agtttccttt tttattctct 4020
caagccacca gctgccagcc accagcagcc agctgccagc ctagcttttt tttttttttt 4080 tttttttag cacttagtat ttagcattta ttaacaggta ctctaagaat gatgaagcat 4140
tgtttttaat cttaagacta tgaaggtttt tcttagttct tctgcttttg caattgtgtt 4200
tgtgaaattt gaatacttgc aggctttgta tgtgaataat tctagcgggg gacctgggag 4260
ataattccta cggggaattc ttaaaactgt gctcaactat taaaatgaat gagctttcaa 4320
aaaaaaaaaa aaaaaaaaaa aaaaaaaaaa aaa 4353

<210> SEQ ID NO 3
<211> LENGTH: 570
<212> TYPE: PRT
<213> ORGANISM: Mus musculus

<400> SEQUENCE: 3

Met Gly Asn Trp Ala Val Asn Glu Gly Leu Ser Ile Phe Val Ile Leu
1 5 10 15

Val Trp Leu Gly Leu Asn Val Phe Leu Phe Ile Asn Tyr Tyr Lys Val
20 25 30

Tyr Asp Asp Gly Pro Lys Tyr Asn Tyr Thr Arg Lys Leu Leu Gly Ser
35 40 45

Ala Leu Ala Leu Ala Arg Ala Pro Ala Ala Cys Leu Asn Phe Asn Cys
50 55 60

Met Leu Ile Leu Leu Pro Val Cys Arg Asn Leu Leu Ser Phe Leu Arg
65 70 75 80

Gly Ser Ser Ala Cys Cys Ser Thr Arg Ile Arg Arg Gln Leu Asp Arg
85 90 95

Asn Leu Thr Phe His Lys Met Val Ala Trp Met Ile Ala Leu His Thr
100 105 110

Ala Ile His Thr Ile Ala His Leu Phe Asn Val Glu Trp Cys Val Asn
115 120 125

Ala Arg Val Gly Ile Ser Asp Arg Tyr Ser Ile Ala Leu Ser Asp Ile
130 135 140

Gly Asp Asn Glu Asn Glu Glu Tyr Leu Asn Phe Ala Arg Glu Lys Ile
145 150 155 160

Lys Asn Pro Glu Gly Gly Leu Tyr Val Ala Val Thr Arg Leu Ala Gly
165 170 175

Ile Thr Gly Ile Val Ile Thr Leu Cys Leu Ile Leu Ile Ile Thr Ser
180 185 190

Ser Thr Lys Thr Ile Arg Arg Ser Tyr Phe Glu Val Phe Trp Tyr Thr
195 200 205

His His Leu Phe Val Ile Phe Phe Ile Gly Leu Ala Ile His Gly Ala
210 215 220

Glu Arg Ile Val Arg Gly Gln Thr Ala Glu Ser Leu Glu Glu His Asn
225 230 235 240

Leu Asp Ile Cys Ala Asp Lys Ile Glu Glu Trp Gly Lys Ile Lys Glu

-continued

```
                245                 250                 255

Cys Pro Val Pro Lys Phe Ala Gly Asn Pro Pro Met Thr Trp Lys Trp
            260                 265                 270

Ile Val Gly Pro Met Phe Leu Tyr Leu Cys Glu Arg Leu Val Arg Phe
        275                 280                 285

Trp Arg Ser Gln Gln Lys Val Val Ile Thr Lys Val Val Thr His Pro
    290                 295                 300

Phe Lys Thr Ile Glu Leu Gln Met Lys Lys Lys Gly Phe Lys Met Glu
305                 310                 315                 320

Val Gly Gln Tyr Ile Phe Val Lys Cys Pro Lys Val Ser Lys Leu Glu
                325                 330                 335

Trp His Pro Phe Thr Leu Thr Ser Ala Pro Glu Glu Asp Phe Phe Ser
            340                 345                 350

Ile His Ile Arg Ile Val Gly Asp Trp Thr Glu Gly Leu Phe Asn Ala
        355                 360                 365

Cys Gly Cys Asp Lys Gln Glu Phe Gln Asp Ala Trp Lys Leu Pro Lys
    370                 375                 380

Ile Ala Val Asp Gly Pro Phe Gly Thr Ala Ser Glu Asp Val Phe Ser
385                 390                 395                 400

Tyr Glu Val Val Met Leu Val Gly Ala Gly Ile Gly Val Thr Pro Phe
                405                 410                 415

Ala Ser Ile Leu Lys Ser Val Trp Tyr Lys Tyr Cys Asp Asn Ala Thr
            420                 425                 430

Ser Leu Lys Leu Lys Lys Ile Tyr Phe Tyr Trp Leu Cys Arg Asp Thr
        435                 440                 445

His Ala Phe Glu Trp Phe Ala Asp Leu Leu Gln Leu Leu Glu Thr Gln
    450                 455                 460

Met Gln Glu Arg Asn Asn Ala Asn Phe Leu Ser Tyr Asn Ile Tyr Leu
465                 470                 475                 480

Thr Gly Trp Asp Glu Ser Gln Ala Asn His Phe Ala Val His His Asp
                485                 490                 495

Glu Glu Lys Asp Val Ile Thr Gly Leu Lys Gln Lys Thr Leu Tyr Gly
            500                 505                 510

Arg Pro Asn Trp Asp Asn Glu Phe Lys Thr Ile Ala Ser Glu His Pro
        515                 520                 525

Asn Thr Thr Ile Gly Val Phe Leu Cys Gly Pro Glu Ala Leu Ala Glu
    530                 535                 540

Thr Leu Ser Lys Gln Ser Ile Ser Asn Ser Glu Ser Gly Pro Arg Gly
545                 550                 555                 560

Val His Phe Ile Phe Asn Lys Glu Asn Phe
                565                 570
```

<210> SEQ ID NO 4
<211> LENGTH: 9
<212> TYPE: PRT
<213> ORGANISM: Homo sapiens

<400> SEQUENCE: 4

```
Cys Ser Thr Arg Val Arg Arg Gln Leu
1               5
```

<210> SEQ ID NO 5
<211> LENGTH: 18
<212> TYPE: PRT
<213> ORGANISM: Artificial Sequence
<220> FEATURE:

<223> OTHER INFORMATION: Human Nox2ds with tat

<400> SEQUENCE: 5

Arg Lys Lys Arg Arg Gln Arg Arg Arg Cys Ser Thr Arg Val Arg Arg
1 5 10 15

Gln Leu

<210> SEQ ID NO 6
<211> LENGTH: 9
<212> TYPE: PRT
<213> ORGANISM: Mus musculus

<400> SEQUENCE: 6

Cys Ser Thr Arg Ile Arg Arg Gln Leu
1 5

<210> SEQ ID NO 7
<211> LENGTH: 18
<212> TYPE: PRT
<213> ORGANISM: Artificial Sequence
<220> FEATURE:
<223> OTHER INFORMATION: Mouse Nox2ds with tat

<400> SEQUENCE: 7

Arg Lys Lys Arg Arg Gln Arg Arg Arg Cys Ser Thr Arg Ile Arg Arg
1 5 10 15

Gln Leu

<210> SEQ ID NO 8
<211> LENGTH: 20
<212> TYPE: PRT
<213> ORGANISM: Mus musculus

<400> SEQUENCE: 8

Gly Ser Ser Ala Cys Cys Ser Thr Arg Ile Arg Arg Gln Leu Asp Arg
1 5 10 15

Asn Leu Thr Phe
20

<210> SEQ ID NO 9
<211> LENGTH: 23
<212> TYPE: PRT
<213> ORGANISM: Artificial Sequence
<220> FEATURE:
<223> OTHER INFORMATION: Nox2ds alternate with tat

<400> SEQUENCE: 9

Arg Lys Lys Arg Arg Gln Arg Arg Arg Phe Ala Val His His Asp Glu
1 5 10 15

Glu Lys Asp Val Ile Thr Gly
20

<210> SEQ ID NO 10
<211> LENGTH: 16
<212> TYPE: PRT
<213> ORGANISM: Artificial Sequence
<220> FEATURE:
<223> OTHER INFORMATION: Nox2 inhibitor with tat

<400> SEQUENCE: 10

Arg Lys Lys Arg Arg Gln Arg Arg Arg Arg Gly Val His Phe Ile Phe
1 5 10 15

-continued

```
<210> SEQ ID NO 11
<211> LENGTH: 23
<212> TYPE: PRT
<213> ORGANISM: Artificial Sequence
<220> FEATURE:
<223> OTHER INFORMATION: Nox2 inhibitor with tat

<400> SEQUENCE: 11

Arg Lys Lys Arg Arg Gln Arg Arg Arg Gln Arg Arg Arg Gln Ala Arg
1               5                   10                  15

Pro Gly Pro Gln Ser Pro Gly
            20


<210> SEQ ID NO 12
<211> LENGTH: 9
<212> TYPE: PRT
<213> ORGANISM: Artificial Sequence
<220> FEATURE:
<223> OTHER INFORMATION: Scrambled Nox2ds

<400> SEQUENCE: 12

Cys Leu Arg Val Thr Arg Gln Ser Arg
1               5


<210> SEQ ID NO 13
<211> LENGTH: 9
<212> TYPE: PRT
<213> ORGANISM: Homo sapiens

<400> SEQUENCE: 13

Arg Lys Lys Arg Arg Gln Arg Arg Arg
1               5
```

THERAPEUTIC USE OF PEPTIDE INHIBITORS OF NADPH OXIDASE; AEROSOLIZATION AS A DELIVERY MECHANISM

CROSS REFERENCE TO RELATED APPLICATIONS

This application is a Continuation of U.S. patent application Ser. No. 13/473,758, filed May 17, 2012 and issued as U.S. Pat. No. 8,962,570, which claims the benefit of U.S. Provisional Application No. 61/486,837, filed May 17, 2011, entitled "Therapeutic Use of Peptide Inhibitors of NADPH Oxidase; Aerosolization as a Delivery Mechanism," each of which is incorporated herein by reference in its entirety.

STATEMENT REGARDING FEDERAL FUNDING

This invention was made with government support under Grant No. HL079207 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 6527_121468_ST25.txt. The size of the text file is 18,152 bytes, and the text file was created on May 16, 2012.

Methods of using polypeptide inhibitors of NADPH Oxidase are provided.

The NADPH Oxidase (nicotinamide adenine dinucleotide phosphate-oxidase, Nox) family of enzymes emerged during the evolutionary transition from unicellular to multicellular organisms and catalyze the reduction of oxygen ($O_2$) to superoxide ($O_2^-$). Nox2 is a member of the Nox family and is known by a variety of aliases, including CYBB (Cytochrome b-245, beta polypeptide (chronic granulomatous disease)). Aliases of Nox2 include: CYBB, AMCBX2; CGD; GP91-1; GP91-PHOX; GP91PHOX; and p91-PHOX. An exemplary amino acid sequence of Nox2 is provided in FIG. 1A (SEQ ID NO: 1, GenBank Accession No. NP_000388.2, see also: GenBank Accession No. NM_000.397.3 (SEQ ID NO: 2, FIG. 1B) and GenBank Accession No. NP-031833.3 (SEQ ID NO: 3, FIG. 1C, murine Nox2), providing an exemplary cDNA sequence for Nox2; OMIM 300481; and Gene ID 1536). Nox2 is also referred to as the phagocytic "respiratory burst oxidase" for its role in the innate immune response, specifically in phagocyte killing of ingested microbes. A mutation in Nox2 results in the inability of phagocytes to kill ingested microbes in X-linked chronic granulomatous disease (CGD, see, e.g., OMIM 306400)—a disease that results in susceptibility of humans to pulmonary infections, including enteric bacteria, *Staphylococcus, Aspergillus pneumoniae* and *Burkholderia cepacia* infections (See, e.g., Griffith et al. (2009) Nox Enzymes and Pulmonary Disease, *Antioxidants and Redox Signaling* 11(10):2505-2516).

Paradoxically, the adaptation of the Nox enzymes as part of the innate immune system also results in detrimental consequences in the presence of persistent or overwhelming, infectious or non-infectious environmental stressors. Nox2 action is considered to be a significant factor in pulmonary hypertension, especially in hypoxic states, such as with obstructive sleep apnea, and ischemia/repurfusion injury, for instance after lung transplantation, obstructive lung disorders, such as chronic obstructive pulmonary disease, asthma, cystic fibrosis and emphysema, pulmonary fibrosis and lung cancer (Griffith et al. (2009) *Antioxidants and Redox Signaling* 11(10):2505-2516 and WO 01/017533).

Effective inhibitors of Nox2, and treatments for conditions resulting from the action of Nox2 are desirable.

SUMMARY

It has been surprisingly found that aerosol administration of a polypeptide that is believed to target Nox2 interaction with p47$^{phox}$ has the ability to treat a number of conditions arising from the activity of Nox2, as demonstrated in the Examples below.

Therefore, a method of treating a condition mediated by Nox2 in a patient is provided. The method comprises administering to the patient by inhalation a polypeptide comprising a fragment of SEQ ID NO: 1 that comprises the amino acid sequence CSTRVRRQL (SEQ ID NO: 4), or a derivative thereof having a single amino acid substitution and comprising the sequence CSTRIRRQL (SEQ ID NO: 6). The polypeptide is able to decrease superoxide production by Nox2, in an amount and for a duration effective to relieve one or more symptoms of the condition in a patient.

The polypeptide is optionally connected to a Cell-penetration peptide sequence, such as a tat sequence. According to certain non-limiting embodiments, the polypeptide consists essentially of, or consists of one or more of CSTRVRRQL (SEQ ID NO: 4); RKKRRQRRRCSTRVRRQL (SEQ ID NO: 5); CSTRIRRQL (SEQ ID NO: 6); and RKKRRQRRRCSTRIRRQL (SEQ ID NO: 7).

Conditions treatable according to the methods include one or more of: right ventricular hypertrophy; pulmonary hypertension; acute lung injury; obstructive sleep apnea; ischemia/reperfusion injury in the lung or elsewhere; pulmonary fibrosis; an obstructive lung disorder, such as one or more of Chronic Obstructive Pulmonary Disease, asthma, cystic fibrosis and emphysema; atherosclerosis; inflammation; and a neurodegenerative disease, such as Alzheimer's disease.

Likewise, a method of decreasing superoxide production in a patient also is provided, with the end result of reducing one or more symptoms of a condition, for example and without limitation as described herein. The method comprises administering to the patient by inhalation a polypeptide comprising a fragment of SEQ ID NO: 1 that comprises the amino acid sequence CSTRVRRQL (SEQ ID NO: 4), or a derivative thereof having a single amino acid substitution and comprising the sequence CSTRIRRQL (SEQ ID NO: 6), and wherein the polypeptide is able to decrease superoxide production by Nox2, in an amount and for a duration effective to decrease superoxide production by Nox2 in a patient.

BRIEF DESCRIPTION OF THE DRAWINGS

FIGS. 1A and 1B provide a Nox2 amino acid sequence (GenBank Accession No. NP_000388.2, SEQ ID NO: 1) and mRNA sequence (GenBank Accession No. NM_000.397.3, SEQ ID NO: 2), respectively. FIG. 1C provides the murine Nox2 amino acid sequence (GenBank Accession No. NP_031833.3, SEQ ID NO: 3).

FIG. 7 (top panel) is a graph showing right ventricular pressure and FIG. 7 (bottom panel) is a graph showing the Fulton's Index for the mice tested.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings and "mammal" refers to all mammals, including, but not limited to human beings.

Unless indicated otherwise, all nucleotide sequences are provided in 5' to 3' orientation and all amino acid sequences are provided in N-terminal to C-terminal orientation.

Numerous reports demonstrate the contribution of vascular isoforms of the phagocyte NADPH oxidase (Nox1, Nox2 and Nox4) to the pathogenesis of conditions, such as neurodegenerative, cardiovascular and cardiopulmonary disorders. It is increasingly becoming clear that development of therapeutic compounds that selectively inhibit NADPH oxidase isoforms have important therapeutic potential.

Figure 2A:
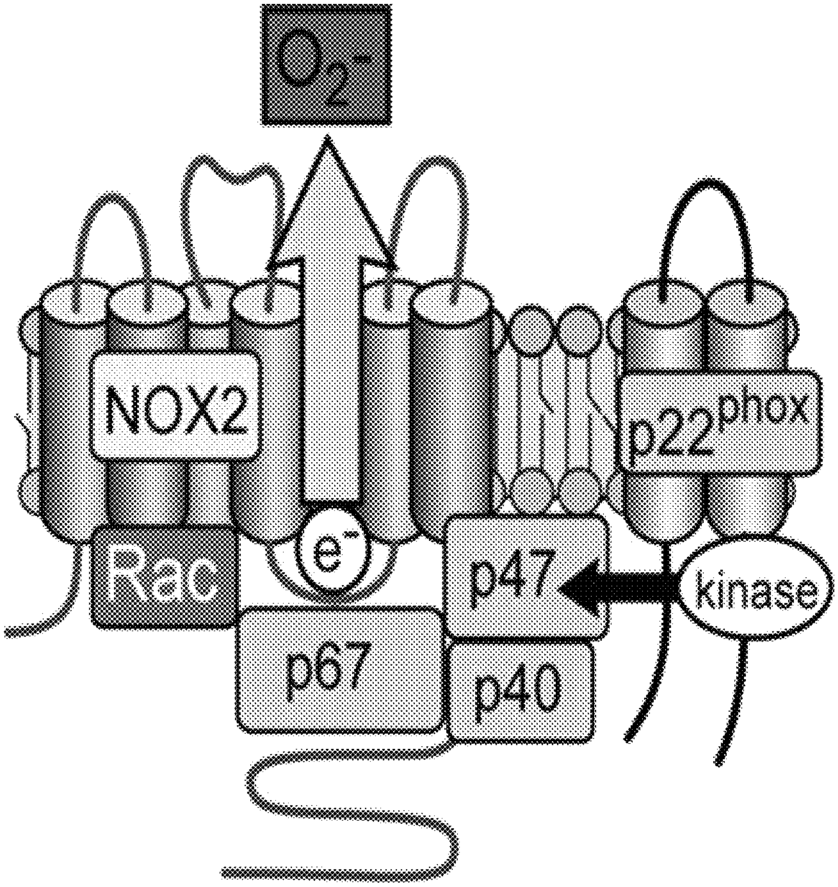
FIG. 2A is a schematic diagram depicting an activated Nox2 complex and FIG. 2B is a schematic diagram depicting a proposed mechanism for the interference of Nox2 activity by a Nox2ds peptide described herein, showing that binding of Nox2ds to p47$^{phox}$ inhibits NADPH oxidase activity by blocking the translocation of cytosolic components.
Figure 2B:
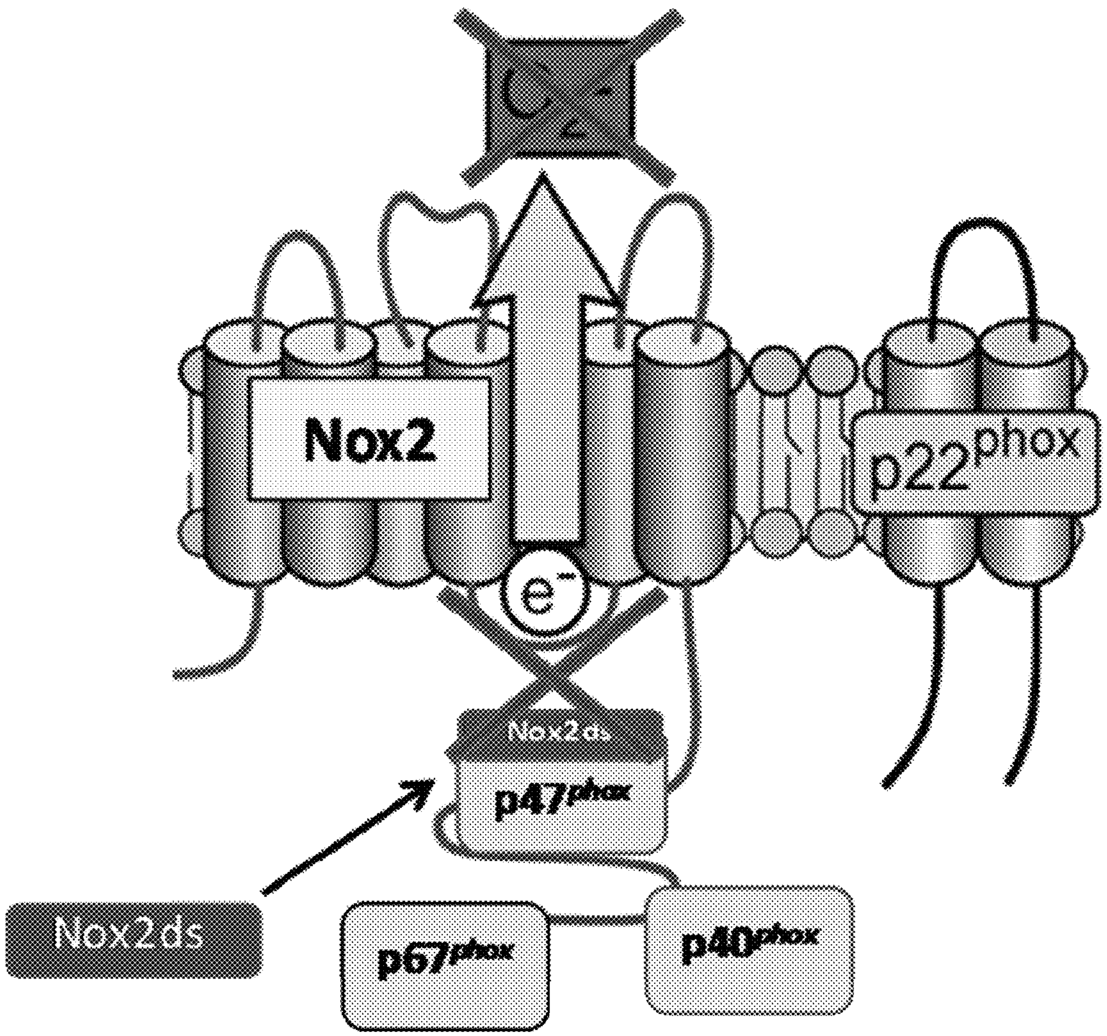

A Nox2 B-loop peptide, Nox2 docking sequence (Nox2ds), is shown herein to effectively inhibit NADPH oxidase and attenuate the progression of cardiovascular diseases. Nox2ds was designed to inhibit the association of Nox2 with $p47^{phox}$ and thus selectively inhibit Nox2-oxidase. FIG. 2A shows the activated Nox2 complex and FIG. 2B shows a proposed mechanism for the interference of Nox2 activity by a Nox2ds peptide described herein.

The delivery of polypeptides (peptides or amino acid sequences having two or more amino acids, and including as a class oligopeptides, peptides, protease-protected peptides, peptidomimetics, peptides delivered with a variety of nanotechnology formulations for improved efficacy, etc.) for therapeutic use presents limitations due to the poor oral bioavailability. Here we describe an effective mechanism for delivery of our novel and specific oxidase inhibitor that can potentially be easily adapted for clinical use.

Provided therefore are methods of treating a condition mediated by Nox2 in a patient. Non-limiting examples of conditions mediated by Nox2 are conditions of the heart, lungs and blood vessels connecting the heart and lungs that results from or is exacerbated by activity of Nox2, including, without limitation, one or more of: right ventricular hypertrophy; pulmonary hypertension; acute lung injury; obstructive sleep apnea; ischemia/reperfusion injury in the lung; pulmonary fibrosis; an obstructive lung disorder such as Chronic Obstructive Pulmonary Disease (COPD), asthma, cystic fibrosis and emphysema; and atherosclerosis (See, e.g., Judkins, C P et al., Direct evidence of a role for Nox2 in superoxide production, reduced nitric oxide bioavailability, and early atherosclerotic plaque formation in $ApoE^{-/-}$ mice (2010) *Am J Physiol Heart Circ. Physiol* 298:H24-H32; Madamanchi, N R, NADPH Oxidases and atherosclerosis: Unraveling the Details (2010) *Am J Physiol Heart Circ. Physiol* 298:H1-H2; and Griffith et al. (2009) *Antioxidants and Redox Signaling* 11(10):2505-2516).

The method comprises administering to the patient by inhalation a polypeptide that inhibits Nox2 activity, thereby relieving one or more symptoms of the condition in a patient. Polypeptides useful for the methods described herein are described below, and also are described earlier in International Patent Publication No. WO 01/017533. The polypeptides are believed to act as a decoy for $p47^{phox}$ binding to Nox2, such that the presence of the polypeptide interferes with $p47^{phox}$ binding to Nox2, thereby decreasing production of superoxide by Nox2.

According to one example, the polypeptides are fragments (incomplete portions) of SEQ ID NO: 1 that comprises the amino acid sequence CSTRVRRQL (SEQ ID NO: 4), or a derivative thereof having a single amino acid substitution and comprising the sequence CSTRIRRQL (SEQ ID NO: 5), optionally linked to a cell permeation polypeptide such as tat. Non-limiting examples of useful polypeptides include:

```
                                        (SEQ ID NO: 4)
Nox2ds: CSTRVRRQL
(aka human gp91ds in some publications);

                                        (SEQ ID NO: 5)
Nox2ds-tat: RKKRRQRRRCSTRVRRQL
(aka human gp91ds-tat in some publications);

                                        (SEQ ID NO: 6)
gp91ds: CSTRIRRQL;
and

                                        (SEQ ID NO: 7)
gp91ds-tat: RKKRRQRRRCSTRIRRQL.
```

One or more additional contiguous flanking amino acids to the CSTRVRRQL (SEQ ID NO: 2) sequence of SEQ ID NO: 1 (FIG. 1A) or one or more additional contiguous flanking amino acids to the CSTRIRRQL (SEQ ID NO: 6) sequence of SEQ ID NO: 3 (FIG. 1C) may be present in the polypeptide so long as the function of the polypeptide is not impracticably reduced. For example and without limitation, the polypeptide may consist of a contiguous fragment of SEQ ID NO: 1 from 9-200, or more amino acids in length, optionally containing the sequence CSTRIRRQL (SEQ ID NO: 6) instead of the sequence CSTRVRRQL (SEQ ID NO: 4). Exemplary, and non-limiting examples of such polypeptides include:

```
GSSACCSTRVRRQLDRNLTF, (SEQ ID NO: 1, bases 81-100);

GSSACCSTRVRRQL, (SEQ ID NO: 1, bases 81-94);

CSTRVRRQLDRNLTF, (SEQ ID NO: 1, bases 86-100);

SACCSTRVRRQLDRNL, (SEQ ID NO: 1, bases 83-98);

CCSTRVRRQLD, (SEQ ID NO: 1, bases 85-95);

VCRNLLSFLRGSSACCSTRVRRQLDRNLTF, (SEQ ID NO: 1,
bases 71-100);

GSSACCSTRVRRQLDRNLTFHKMVAWMIAL, (SEQ ID NO: 1,
bases 81-110);

GSSACCSTRIRRQLDRNLTF, (SEQ ID NO: 8);
and

CCSTRIRRQLD, (SEQ ID NO: 8, bases 5-15).
```

As one of ordinary skill would recognize, this list is far from complete, with two possible 9-mers (CSTRIRRQL (SEQ ID NO: 6) and CSTRVRRQL (SEQ ID NO: 4)), four possible 10-mers; six possible 11-mers, eight possible 12-mers, etc. Likewise, for example and without limitation, the polypeptide may consist of a contiguous fragment of SEQ ID NO: 3 from 9-200, or more amino acids in length, optionally containing the sequence CSTRVRRQL (SEQ ID NO: 4) instead of the sequence CSTRIRRQL (SEQ ID NO: 6). Similarly, the polypeptide optionally comprises 3, 4, 5, 6, 7 or 8 contiguous amino acids of SEQ ID NOs 3 or 5 and one or more flanking amino acids of CSTRVRRQL (SEQ ID NO: 4) or CSTRIRRQL (SEQ ID NO: 6) found in SEQ ID NOs: 1 and 3, respectively. Despite the number of permutational possibilities, the size and sequence of the polypeptide may be limited by practical issues, such as cost of synthesis, solubility, etc. In any case, the ability of any polypeptide to inhibit superoxide production by Nox2 is readily tested by one of ordinary skill using the methods described in the examples below.

As indicated above, the polypeptide may be linked, e.g. covalently, to a cell penetrating peptide. Cell-Penetrating Peptides (CPPs) are also known as protein transduction domains (PTDs), membrane translocating sequences (MTSs), and Trojan peptides. They are short peptides (40 amino acids), with the ability to access the interior of almost any cell. They typically are highly cationic and usually rich in arginine and lysine amino acids. They are thought to use several mechanisms, including direct translocation across the plasma membrane and endocytosis to enter cells and can transport a variety of covalently and noncovalently conjugated "cargoes" such as proteins. Polypeptides often are linked to cell penetrating peptides via a peptide bond in that the CPP is part of a contiguous amino acid sequence, as with the Nox2ds-tat polypeptide shown above. Cell penetrating peptides are broadly known, the prototypical example of which is the HIV tat peptide. Their use and usefulness is well-understood by those of ordinary skill (See, e.g., Sebbage V, Cell Penetrating Peptides and Their Therapeutic Applications *Bioscience Horizons* 2(1):64-72 (2009)). As indicated in that reference, examples of CPPs include, without limitation: HIV tat, oligoarginine, p-antp, plsl, transportan, MPG Pβ and pα and Pep-1 sequences. CPP sequences are broadly known and a number of commercial polypeptide synthesis vendors offer the option of incorporating a CPP into a synthesized peptide.

Alternate peptides for use in the methods described herein include:

```
                                          (SEQ ID NO: 9)
RKKRRQRRRFAVHHDEEKDVITG;

                                         (SEQ ID NO: 10)
RKKRRQRRRRGVHFIF;
and

an alternative chimeric sequence containing
tat plus a region of p47phox:
                                         (SEQ ID NO: 11)
RKKRRQRRRQRRRQARPGPQSPG.
```

According to one non-limiting example, the compounds described herein are formulated into a composition with one or more pharmaceutical vehicles or diluents for inhalation therapy. The composition can be formulated in a classical manner using solid or liquid vehicles, diluents and additives appropriate to the mode of administration. The composition may be delivered by any suitable inhalation delivery system, for example and without limitation, a nebulizer or atomizer, a dry powder inhaler, a nasal inhaler and a metered dose aerosol inhaler, as are broadly known in the pharmaceutical arts. Therapeutic/pharmaceutical compositions are prepared in accordance with acceptable pharmaceutical procedures and practices, such as are described in Sciarra et al., "Aerosols", in *Remington: The Science and Practice of Pharmacy,* 21st edition, Eds. Paul Beringer et al., Lippincott, Williams & Wilkins, Baltimore, Md. Easton, Pa. (2005) pp. 1000-1017, describing a variety of inhalation devices and methods useful in the methods described herein.

In any case, as used herein, any agent or agents used for treating a condition mediated by Nox2 in a patient is administered in an amount and for a duration effective to relieve one or more symptoms of the condition. A "symptom" being an effect of the condition that can be ascertained, including subjective symptoms, such as pain, and objective symptoms, such as vascular stenosis, cardiac wall thickness and blood pressure. According to one non-limiting embodiment, effective doses range from but are not limited to 0.5 to 50 mg per inhaled dose, delivered, for example and without limitation, in 5 ml at a rate of 8 L/min over 20 min, to delivered an airway concentration of, for example ~1 μM each 3 days over an extended period including but not limited to 3 weeks, one month, two months, six months, etc. Higher or lower doses may be administered as is needed to achieve a therapeutic objective. For each compound described herein, an effective dose or dose range is expected to vary from that of other compounds described herein for any number of reasons, including the molecular weight of the compound, bioavailability in the dosage form, route of administration, solubility of the compound in a given excipient (e.g., carrier or vehicle), specific activity (e.g., $EC_{50}$), etc. In any case, the effective range (e.g., the therapeutic window) between the minimally-effective dose, and maximum tolerable dose in a subject can be determined empirically by a person of skill in the art, with end points being determinable by in vitro and in vivo assays, such as those described herein and/or are acceptable in the pharmaceutical and medical arts for obtaining such information regarding agents, such as inhalable compounds. Different concentrations of the agents described herein are expected to achieve similar results. The compounds can be administered one or more times daily, for example two to four times daily, once every two, three, four, five or more days, weekly, monthly, etc., including increments therebetween. It is possible to deliver the drug continuously, for instance in severe cases, or substantially continuously as in the case of, for example, by nebulization. A person of ordinary skill in the pharmaceutical and medical arts will appreciate that it will be a matter of design choice and/or optimization to identify a suitable dosage regimen for improving symptoms of a condition.

Any of the compounds described herein may be compounded or otherwise manufactured into a suitable composition for use, such as a pharmaceutical dosage form or drug product in which the compound is an active ingredient. Compositions may comprise a pharmaceutically acceptable carrier, vehicle or excipient. An excipient is an inactive substance used as a carrier or vehicle for the active ingredients of a medication. Although "inactive," excipients may facilitate and aid in increasing the delivery, stability or bioavailability of an active ingredient in a drug product. Non-limiting examples of useful excipients for inhalable dosage forms include: rheology modifiers, emulsifiers, oils, buffers, salts, acids, bases, diluents, solvents, propellants, flavors, colorants, preservatives, antioxidants, sorbents, vitamins, sweeteners, etc., as are available in the pharmaceutical/compounding arts. In non-limiting embodiments, the excipient is chosen from water, saline (e.g., normal saline, 0.9% w/v NaCl in water), phosphate-buffered saline and other buffered solutions, dextrose, etc., as are broadly known in the pharmaceutical arts.

Pharmaceutically acceptable salts of any of the compounds described herein also may be used in the methods described herein. Pharmaceutically acceptable salt forms of the compounds described herein may be prepared by conventional methods known in the pharmaceutical arts, and include as a class veterinarily acceptable salts. For example and without limitation, where a compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate; and various organic bases such as piperidine, diethanolamine, and N-methylglutamine.

Acid and base addition salts may be prepared by contacting the free base form with a sufficient amount of a desired acid or base to produce the salt in a manner known in the art. The free base may be regenerated by contacting the salt form with a base or acid (depending on the nature of the salt) and isolating the free base. The free base forms differ from their respective salt forms somewhat in certain physical properties such as solubility in polar solvents, but otherwise the salts are equivalent to their respective free base forms for purposes described herein.

Compounds comprising basic nitrogen-containing groups may be quarternized with such agents as $C_{1-4}$ alkyl halides, such as methyl, ethyl, iso-propyl and tert-butyl chlorides, bromides and iodides; $C_{1-4}$ alkyl sulfate such as dimethyl, diethyl and diamyl sulfates; $C_{10-18}$ alkyl halides, such as decyl, dodecyl, lauryl, myristyl and stearyl chlorides, bromides and iodides; and aryl-$C_{1-4}$ alkyl halides, such as benzyl chloride and phenethyl bromide. Such salts permit the preparation of both water-soluble and oil-soluble compounds.

Non-limiting examples of pharmaceutically-acceptable base salts include: aluminum, ammonium, calcium, copper, ferric, ferrous, lithium, magnesium, manganic, manganous, potassium, sodium, and zinc salts. Salts derived from pharmaceutically acceptable organic non-toxic bases include, without limitation: salts of primary, secondary, and tertiary amines, substituted amines including naturally occurring substituted amines, cyclic amines, and basic ion exchange resins, such as arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine(tromethamine).

Acid addition salts may be prepared by treating a compound with pharmaceutically acceptable organic and inorganic acids, including, without limitation: hydrohalides, such as hydrochloride, hydrobromide, hydroiodide; other mineral acids and their corresponding salts such as sulfates, nitrates, and phosphates; alkyl- and mono-arylsulfonates, such as ethanesulfonate, toluenesulfonate, and benzenesulfonate; and other organic acids and their corresponding salts, such as acetate, tartrate, maleate, succinate, citrate, benzoate, salicylate, and ascorbate.

Non-limiting examples of pharmaceutically-acceptable acid salts include: acetate, adipate, alginate, arginate, aspartate, benzoate, besylate (benzenesulfonate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate, galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, and phthalate.

Multiple salt forms are also considered to be pharmaceutically-acceptable salts. Common, non-limiting examples of multiple salt forms include: bitartrate, diacetate, difumarate, dimeglumine, diphosphate, disodium, and trihydrochloride.

As such, "pharmaceutically acceptable salt" as used herein is intended to mean an active ingredient (drug) comprising a salt form of any compound as described herein. The salt form preferably confers to the improved and/or desirable pharmacokinetic/pharmodynamic properties of the compounds described herein.

As indicated above, the described polypeptides are useful for treatment of (that is in relieving or improving one or more symptom of) a condition mediated by Nox2 in a patient, including, without limitation: right ventricular hypertrophy; pulmonary hypertension; acute lung injury; obstructive sleep apnea; ischemia/reperfusion injury; pulmonary fibrosis; an obstructive lung disorder such as Chronic Obstructive Pulmonary Disease (COPD), asthma, cystic fibrosis and emphysema; and atherosclerosis. Other condition mediated by Nox2 in a patient, include, without limitation: pulmonary vascular disease related to left heart failure (systolic and non-systolic heart failure); pulmonary to systemic shunt; systemic to pulmonary circulation shunt; intracardiac shunt; infectious causes (e.g., shistosomiasis, malaria, HIV); hepatopulmonary syndrome; portopulmonary syndrome; chronic renal insufficiency; end stage renal disease; interstitial lung disease; collagen vascular disease (including but not limited to scleroderma, mixed connective tissue disease, rheumatoid arthritis, lupus); exposure to toxins (e.g., toxic rapeseed oil, diet drugs, amphetamine and other sympathomimetics); sleep disordered breathing (obstructive and central); chronic hypoxia (from altitude or intrinsic lung disease); sarcoidosis; thromboembolic disease; and hemolytic blood diseases (e.g.: thallasemia, sickle cell disease). Other conditions that implicate Nox2 include neurodegenerative diseases, such as Alzheimer's disease, Parkinson's disease, and amyotrophic lateral sclerosis (ALS), hypertension, aortic aneurysm, myocardial infarction, arthritis, stroke, cancer, and inflammation. See, generally, Lambeth J D, et al. ((2008) NOX enzymes as novel targets for drug development. Semin Immunopathol. 30(3): 339-63) providing a discussion of many diseases involving Nox2.

Right ventricular hypertrophy (RVH) is a thickening of the right ventricular wall of the heart, and is typically caused by chronic hypertension (high blood pressure) or pulmonary arterial hypertension, which causes the heart muscle to increase in size due to the effort required to pump blood against a higher arterial back-pressure. The disease can also emanate from dysfunction of cardiomyocyte and other heart cells. The right ventricle pumps blood to the lungs, and the thickening of the wall diminishes the internal volume of the ventricle, leading to decreased pumping capacity, and thus lower blood volume delivery to the lungs. However, in conjunction with decreased blood volume, a hypertrophic right ventricle is able to produce higher pressure due to the additional muscle strength. This can lead to further conditions, for example, pulmonary hypertension or hypoxia, or more generalized hypoxemia, which may exacerbate the underlying causes of RVH. Some symptoms of right ventricular hypertrophy include shortness of breath, dizziness, chest pain, increased heart rate, and peripheral edema (swelling of legs, ankles, and feet).

Pulmonary arterial hypertension is an increase in blood pressure in the lungs, specifically in the pulmonary artery and associated vasculature. This can be caused by obstructions or blockages in the heart arteries, caused by bacterial or viral lung infections, lung injury, or other factors causing vasoconstriction including tobacco use, and drug or alcohol abuse. Symptoms include shortness of breath, dizziness, fainting, fatigue, cough, angina, bluing of the skin or lips (cyanosis), and increased heart rate, all of which may be exacerbated by exertion. It can lead to right ventricular hypertrophy (which would contribute to further increases in pulmonary arterial pressure), and heart failure.

Acute lung injury is an umbrella term for a wide range of clinical syndromes whereby an inflammatory immune response, including Nox2 activity, is triggered by any of a number of possible causes. Causes of lung injury may be direct or indirect. Direct causes include major trauma to the lungs, burns, inhalation of smoke or noxious chemicals, aspiration (breathing in stomach contents while vomiting), near drowning, pneumonia, or lung infections. Indirect causes include sepsis (bacterial blood infection), blood transfusion, poisoning, radiation exposure, pancreatitis, heart-lung bypass surgery, head or chest trauma, or severe bleeding due to trauma elsewhere. Inflammation maybe systemic or localized to the lungs, but is characterized by capillary leakage, low lung compliance (reduced change in lung volume per unit change in pressure), pulmonary edema and atelectasis, the latter two causing a decrease in blood gas exchange. Other symptoms include rapid breathing, a sensation of being unable to draw sufficient breath, chest pain, and fever.

Obstructive sleep apnea is a condition whereby the flow of air decreases or pauses during sleep due to the airway becoming narrow, blocked, or floppy. Obstructive sleep apnea is caused by relaxation of the muscles of the upper throat during sleep; a pause in breathing lasting more than 10 seconds is called apnea. Symptoms include heavy snoring that gets louder, followed by a period of silence (during the apnea), and then gasping or snorting as the person attempts to breathe again. It can lead to excessive daytime sleepiness (EDS) due to interrupting the sleep cycle, symptoms of which include irritability, forgetfulness, falling asleep during the day, sleepiness while driving, and persistent headaches. Other risk factors for obstructive sleep apnea include short lower jaw, when compared to upper jaw; certain airway shapes that are narrower or can collapse more easily, large neck size, large tongue, and obesity.

Apnea episodes can decrease blood oxygen (hypoxemia), high blood pressure, heart failure, stroke, and heart arrhythmias, which can lead to other conditions such as pulmonary hypertension, or RVH.

Ischemia is a restriction in blood supply that causes tissue damage in affected areas due to insufficient supply of oxygen and glucose to maintain cellular metabolism. Inadequate blood flow can be caused by vasoconstriction, artery blockage, low blood pressure, septic shock, anemia, or heart failure. Depending on the type of tissue affected, irreversible damage may take occur within 3-5 minutes (e.g., in the brain or heart) or within 10-20 minutes in less aerobically intense organs (e.g., skin). Ischemia leads to the buildup of metabolic waste and cell leakage, and symptoms may include angina, inflammation, mottling or discoloration of skin.

Reperfusion injury can occur when blood flow is reintroduced following ischemia, where the return of oxygen can lead to overproduction of free radicals and reactive oxygen species (ROS), and causing oxidative damage to tissues, for example caused by Nox2 activity. Reperfusion can lead to cardiac arrhythmia, accelerated cell self-destruction, and exaggerated inflammation of tissue already inflamed due to ischemia as white blood cells overreact to tissue damage.

Pulmonary fibrosis is scarring that occurs when lung tissue is damaged. This scarring (fibrosis) makes the lung tissue thicker and stiffer, reducing lung capacity and causing shortness of breath. Symptoms of pulmonary fibrosis include shortness of breath, chronic coughing, fatigue, chest pain, loss of appetite, and weight loss. It can be caused indirectly by other conditions, such as infection, or by direct lung injury or autoimmune conditions. Damage due to pulmonary fibrosis is irreversible, and while it may be managed through palliative care, including oxygen supplementation, or immunosuppression, in some cases a lung transplant is necessary.

Obstructive lung disorders is a category of lung diseases that involve obstruction of airways, which may be caused by inflammation or collapse of airways, and includes, for example: Chronic obstructive pulmonary disease, asthma, cystic fibrosis and emphysema. General symptoms include coughing and wheezing, though other symptoms are particular to specific disorders.

Chronic obstructive pulmonary disease (COPD) is a chronic lung disease that leads to breathing difficulties. It can be chronic bronchitis (a long term, productive cough) or emphysema (lung destruction), or a combination of both. It is most commonly caused by smoking, with other risk factors including inhalation of gases or fumes, exposure to secondhand smoke, or high levels of pollution. Smoke and chemical fumes can cause lung damage, constriction of bronchi, and accumulation of foreign matter (particularly carbon deposits, from smoking) within the lungs, which diminish total lung capacity, and increase breathing difficulty. Symptoms include cough, fatigue, respiratory infections, shortness of breath, and wheezing.

Asthma is caused by inflammation of the airways, which diminishes lung capacity and causes difficulty breathing by restricting airflow. Symptoms of asthma include shortness of breath, chest tightness, wheezing, and coughing. In severe cases, symptoms may include bluing of the face and lips, drowsiness, confusion, rapid pulse, anxiety, and sweating. Asthma attacks may be triggered by animal dander, dust, cold weather, chemical exposure, exercise, mold, pollen, respiratory infection, stress, and smoke.

Cystic fibrosis is a chronic, hereditary disease that causes mucus to become thick and sticky. Most critically, this thick, sticky mucus builds up in the digestive tract, and particularly in the lungs, and becomes a breeding ground for infection. Lung and sinus symptoms include coughing, increased mucus, shortness of breath, fatigue, congestion, recurrent pneumonia (which includes fever, increased coughing, loss of appetite, chest pain, and sinus pain. Cystic fibrosis patients commonly die young due to disabling lung complications.

Emphysema is a progressive condition whereby structural and functional lung tissue is destroyed. This leads to collapsed airways feeding alveoli and, thus, to diminished lung capacity and shortness of breath, expanded chest, hypoxemia, and increased blood carbon dioxide, caused by diminished gas exchange. These effects are compounded as alveoli then die, and lung capillaries close off, leading to lower lung nutrition, which in turn causes a loss of lung elasticity. The majority of emphysema cases are caused by smoking tobacco, though some types occur as a natural symptom of aging, caused by changes in posture, and deterioration of cartilage that holds airways open.

Atherosclerosis is the hardening or stiffening of the arteries, occurring due to the buildup of cholesterol, fat, or other substances, forming deposits ("plaques") in the arteries. Once the plaques reach a sufficient size, they can obstruct blood flow. An added risk is that blood clots may form around the plaques which may become unstable and increase the potential for blockage. Finally, plaques may break off, move into smaller arteries and obstruct them. Artery blockage prevents blood flow to tissue, which can lead to necrosis (tissue death), and may cause heart attack or stroke (if the obstruction moves to the heart), or pulmonary embolism (if the obstruction moves to the lungs). Plaques can also cause weakening of the blood vessels at the plaque site, which can lead to aneurysm, or rupture of an artery. Atherosclerosis does not have any symptoms until blood flow becomes slowed or blocked, which can cause angina, shortness of breath, and symptoms in the intestines, kidneys, legs, or brain, depending on the location of the blockage.

Alzheimer's disease is the most common form of dementia. Loss of memory is typically followed by confusion, irritability, aggression, mood swings, difficulties with language and loss of long-term memory. Death results from loss of bodily functions. The disease is characterized by loss of neurons and synapses in the cerebral cortex and in subcortical regions, resulting in atrophy of the temporal and parietal lobes, the frontal cortex and cingulated gyrus. Using microscopy, amyloid plaques and neurofibrillary tangles can be seen. The mechanism of the disease is currently under vigorous study, however, inflammation, and particularly Nox2 has been implicated in the aggravation of Alzheimer's progression (see, e.g., Park, L, et al. Nox2-Derived Radicals Contribute to neurovascular and Behavioral Dysfunction in Mice Overexpressing the Amyloid Precursor Protein (2007) *Proc. Nat'l. Acad. Sci. U.S.A.* 105(4):1347-1352).

The following are examples and are for illustration purposes.

Example 1

Nox2ds is a Selective Therapeutic Inhibitor of Nox2 NADPH Oxidase

The aim of this study was to test the hypothesis that Nox2ds specifically inhibits reactive oxygen species (ROS) production by Nox2-, but not by Nox1- and Nox4-oxidase. Recent studies suggest that certain amino acid sequences in the B-loop of Nox2, and its corresponding sequences in Nox4, bind to the dehydrogenase domain in the C-terminal tail of Nox2 and Nox4, respectively. This, along with significant homology in these sequence domains among isoforms raised concern for non-isoform-specific effects of Nox2ds (Rey et al., Circ. Res. 2001; Csanyi et al, *Free Radic Biol Med.* 2011 Sep. 15; 51(6):1116-25).

The contribution of vascular isoforms of the NADPH oxidase (Nox1, Nox2 and Nox4) to the pathogenesis of cardiovascular and cardiopulmonary disease, such as pulmonary hypertension, is becoming increasingly clear (See, e.g., Griffith et al. (2009) *Antioxidants and Redox Signaling* 11(10):2505-2516). The development of therapeutics that selectively inhibit these isoforms is an intense area of investigation. Our laboratory originally designed a Nox2 B-loop peptide, Nox2 docking sequence (Nox2ds) that effectively inhibits NADPH oxidase and attenuates the progression of cardiopulmonary disease (WO 01/017533 A1). Nox2ds was designed to target the association of Nox2 with p47phox and thus selectively inhibit Nox2-oxidase. Nevertheless, doubts have been raised about the specificity of Nox2ds. Recent studies suggest that certain amino acid sequences in the B-loop of Nox2, and its corresponding sequences in Nox4, bind to the dehydrogenase domain in the C-terminal tail of Nox2 and Nox4, respectively. This, along with significant homology in these sequence domains among isoforms raised concern for nonisoform-specific effects of Nox2ds. We postulated that Nox2ds specifically inhibits reactive oxygen species production by Nox2-, but not by Nox1 and Nox4-oxidase.

To test this hypothesis, the inhibitory activity of Nox2ds was assessed in cell-free assays using reconstituted systems expressing either Nox1, 2 or 4 oxidase. Nox 2 oxidase was recapitulated by stably transfecting COS 7 cells with Nox2, p22phox, p47phox, and p67phox (aka COS-Nox2). Nox1 oxidase was obtained by transfecting COS 7 cells with Nox1, p22phox, NOXO1 and NOXA1 (COS-Nox1), and Nox 4 oxidase was regenerated by transfection of COS 7 cells with Nox4 and p22phox. Pre-incubation of COS-Nox2 lysates with Nox2ds concentration dependently inhibited superoxide ($O_2^-$) generation as measured by superoxide dismutase-inhibitable reduction of cytochrome c (nmol $O_2^-$/min/$10^7$ lysate-cell equivalents were: 1.33±0.1, 1.36±0.1, 1.05±0.2, 0.83±0.1, 0.82±0.1 and 0.54±0.1, for 0 μM, 0.1

μM, 0.3 μM, 1 μM, 3 μM and 10 μM Nox2ds, respectively). In contrast, the scrambled sequence of Nox2ds (scrmb Nox2ds) did not inhibit Nox2-oxidase (nmol $O_2^-$/min/$10^7$ cell equivalents: 1.44±0.2 for 10 μM scrmb Nox2ds). EPR studies demonstrated that preincubation with Nox2ds, but not its scrambled sequence, inhibited $O_2^-$ production by COS-Nox2 lysates (CM radical intensities were: 36330±2658, 18360±2666 and 34142±6075 for vehicle, 10 μM Nox2ds and 10 μM scrmb Nox2ds, respectively). Pre-incubation of COS-Nox1 lysates with Nox2ds did not inhibit Nox1-derived $O_2^-$ production (nmol $O_2^-$/min/$10^7$ cell equivalents: 0.97±0.14 and 0.765±0.19 for 0 μM and 10 μM Nox2ds, respectively). Moreover, Nox2ds pre-incubation did not inhibit COS-Nox4 lysate H202 production as measured by Amplex red oxidation (nmol $H_2O_2$/min/$10^7$ cell lysate equivalents were: 80.4±3.1, 74.3±2.1, 74.1±5.9, 82.3±3.4 and 83.3±1.6 for 0 μM, 0.1 μM, 0.3 μM, 1 μM and 3 μM Nox2ds, respectively). Preliminary data also suggest that aerosolized Nox2ds peptide markedly attenuates right ventricular hypertrophy in hypoxia-induced pulmonary hypertension in mice (right ventricule/left ventricule+septum ratios were 0.21±0.01, 0.27±0.02 and 0.22±0.004 for normoxic, hypoxic and hypoxic+Nox2ds aerosolized mice, n=2). Our new data support selectivity of Nox2ds peptide in differentiating the contribution of Nox2 vs. Nox1 and Nox4 NADPH oxidase and its potential clinical use in ameliorating cardiopulmonary diseases.

Transfection of Canonical Nox Systems

Cell transfection was carried out using Lipofectamine LTX and Plus reagent (Invitrogen), according to the manufacturer's instructions. COS-22 cells were transiently cotransfected with pcDNA 3.1-hNox1, pCMVsport 6-hNOXA1, and pcDNA3.1-hNoxO1 (COS-Nox1/NOXO1/NOXA1 cells). Cells were used 24 h after transfection. For stable transfection of Nox4, COS-22 cells were transfected with pcDNA3.1/Hygro-hNox4 (COS-Nox4 cells). COS-Nox4 cells were selected in complete medium supplemented with 0.2 mg/ml hygromycin B and 1.8 mg/ml G418. Stable transfectants were maintained in culture under the same conditions. Adherent cells were harvested by incubating with 0.05% trypsin/EDTA for 5 min at 37° C. After addition of DMEM/10% FBS to neutralize the trypsin, the cells were pelleted by centrifugation at 1000 g for 5 min at 4° C. and used for the experiments.

COS-Nox2: COS 7 cells transfected with $p22^{phox}$, Nox2, $p47^{phox}$ and $p67^{phox}$ (M. Dinauer, Indiana University). (Price M O, McPhail L C, Lambeth J D, Han C H, Knaus U G, Dinauer M C. Blood. 2002 Apr. 15; 99(8):2653-61.)

ROS Detection in Cell-Free Systems

Superoxide-Generating Activity:

Superoxide ($O_2^-$) production was measured in COS-Nox1 and COS-Nox2 lysates by determining the rate of $O_2^-$ dismutase (SOD) inhibitable cytochrome c reduction and by electron paramagnetic resonance (EPR).

Cytochrome c Assay:

COS-Nox2, COS-Nox1/NOXO1/NOXA1, and COS-22 cells were suspended to a concentration of $5\times10^7$ cells/ml in ice-cold disruption buffer (8 mM potassium, sodium phosphate buffer, pH 7.0, 131 mM NaCl, 340 mM sucrose, 2 mM $NaN_3$, 5 mM $MgCl_2$, 1 mM EGTA, 1 mM EDTA, and protease inhibitor cocktail) [31]. The cells were lysed by five freeze/thaw cycles and passed through a 30-gauge needle five times to further lyse the cells. Cell disruption was confirmed by phase-contrast microscopy. The cell lysate was centrifuged at 1000 g for 10 min at 4° C. to remove unbroken cells, nuclei, and debris. Throughout all these procedures, extreme care was taken to maintain the lysate at a temperature close to 0° C. Superoxide production was calculated from the initial linear rate (over 10 min) of SOD-inhibitable cytochrome c reduction quantified at 550 nm using the extinction coefficient of 21.1 mM-1 cm-1 (Biotek Synergy 4 hybrid multimode microplate reader). The oxidase assay buffer consisted of 65 mM sodium phosphate buffer (pH 7.0), 1 mM EGTA, 10 μM FAD, 1 mM $MgCl_2$, 2 mM $NaN_3$, and 0.2 mM cytochrome c. The components of the cell-free system were added in the following order: oxidase assay buffer, cell lysate ($5\times10^5$ cell equivalents/well), and Nox2ds/Scrmb Nox2ds peptides at a final concentration of 0.1, 0.3, 1.0, 3.0, and 10 μM. The plates were placed on an orbital shaker to mix contents for 5 min at 120 movements/min at room temperature. LIDS, an established lipid activator of phagocyte cell-free systems, was added at a concentration of 130 μM, and $O_2^-$ production was initiated by the addition of 180 μM NADPH. The concentration of Nox2ds peptide that caused 50% inhibition of $O_2^-$ production ($IC_{50}$) in COS-Nox2 cell lysates was calculated by Prism 5 (GraphPad Software, La Jolla, Calif., USA).

Electron Paramagnetic Resonance:

The spin probe 1-hydroxy-3-methoxycarbonyl-2,2,5,5-tetramethylpyrrolidine hydrochloride (CMH; Alexis Corp., San Diego, Calif., USA) was used to examine $O_2^-$ production in COS-Nox2 cell lysates using a Bruker eScan table-top EPR spectrometer (Bruker Biospin, USA). Superoxide production was measured in oxidase assay buffer (65 mM sodium phosphate buffer, pH 7.0, 1 mM EGTA, 10 μM FAD, 1 mM $MgCl_2$, 2 mM $NaN_3$) supplemented with 50 μM CMH. Cell lysates ($5\times10^5$ cell equivalents) were incubated with Nox2ds and Scrmb Nox2ds peptides for 5 min at room temperature. After the preincubation period, LiDS was added at a concentration of 130 μM and $O_2^-$ production was initiated by the addition of 180 μM NADPH. Analyses of the EPR spectra peak heights were used to quantify the amount of $O_2^-$ produced by the lysates and were compared with buffer-only control spectra or spectra in the presence of 10 μM Nox2ds, 10 μM Scrmb Nox2ds, or 150 U/ml SOD. The effects of Nox2ds and Scrmb Nox2ds were expressed as SOD-inhibitable formation of CM. radical. To minimize the deleterious effects of contaminating metals, the buffers were treated with Chelex resin and contained 25 μM deferoxamine (Noxygen Science Transfer, Germany).

$H_2O_2$-Generating Activity:

Hydrogen peroxide ($H_2O_2$) generation was quantified in COS-Nox4 cell lysates by Amplex Red. $H_2O_2$-producing activity was quantified in intact COS-Nox4 cells using Amplex red. Briefly, COS-Nox4 cells ($5\times10^7$ cells/nil) were disrupted in ice-cold disruption buffer (PBS containing 0.1 mM EDTA, 10% glycerol, protease inhibitor cocktail, and 0.1 mM PMSF) by freeze/thaw cycles as we described above. Incubation of COS-Nox4 cell lysate with Nox2ds was performed in assay buffer (25 mM Hepes, pH 7.4, containing 0.12 M NaCl, 3 mM KCl, 1 mM MgCl2, 0.1 mM Amplex red, and 0.32 U/ml HRP) for 5 min at room temperature on an orbital shaker (120 movements/min), before the addition of 36 μM NADPH, to initiate $H_2O_2$ production. This concentration of NADPH was used because it was found that higher concentrations interfered with Amplex red fluorescence. Fluorescence measurements were made using a Biotek Synergy 4 hybrid multimode microplate reader with a 530/25-excitation and a 590/35-emission filter. A standard curve of known $H_2O_2$ concentrations was developed using the Amplex red assay (as per the manufacturer's instructions) and was used to quantify $H_2O_2$ production in the COS-Nox4 cell-free system. Nox4 activity was obtained by subtracting nontransfected COS-22 cell lysate activity from COS-Nox4 cell lysate activity. The reaction was monitored at room temperature for 10 min, and the emission increase was linear during this interval.

Peptide Sequences:

Peptides were synthesized with an amide in the carboxy terminus.

```
                                        (SEQ ID NO: 4)
Nox2ds: CSTRVRRQL

                                        (SEQ ID NO: 12)
Scrmb Nox2ds (Scrambled Nox2ds): CLRVTRQSR
```

Figure 3A:
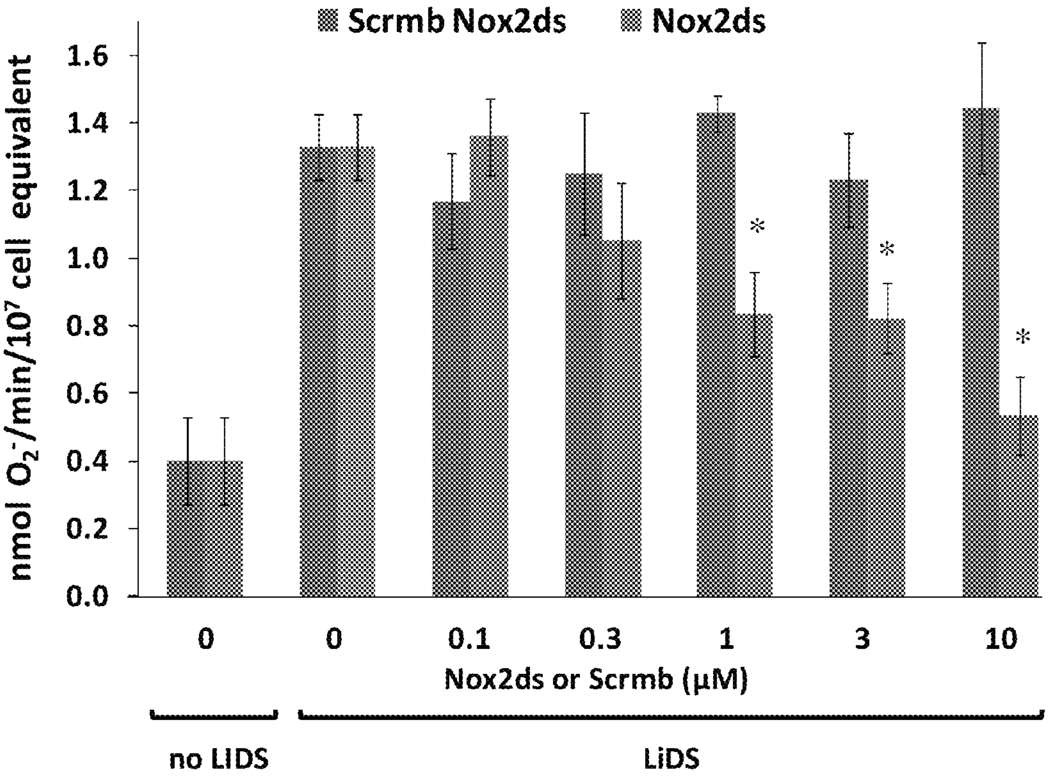
FIG. 3A is a graph showing the rate of $O_2^-$ production in COS-Nox2 lysates pretreated with Nox2ds or scrambled control (Scrmb Nox2ds). $O_2^-$ production was initiated by the addition of NADPH and measured by the SOD-inhibitable cytochrome c reduction for 10 min.

Nox2ds, but not Scrambled Peptide, Attenuates $O_2^-$ Production in COS-Nox2 Lysates Cytochrome C Assay. FIG. 3A. Rate of $O_2^-$ production in COS-Nox2 lysates pretreated with Nox2ds or scrambled control (Scrmb Nox2ds). $O_2^-$ production was initiated by the addition of NADPH and measured by the SOD-inhibitable cytochrome c reduction for 10 min. These data confirm the ability of the Nox2 oxidase system to produce $O_2^-$ and of Nox2ds to sequence-specifically inhibit the Nox2 enzyme. Concentration-dependent inhibition $O_2$ production by Nox2 was demonstrated for Nox2ds but not its scrambled counterpart (Scrmb).

Figure 3B:
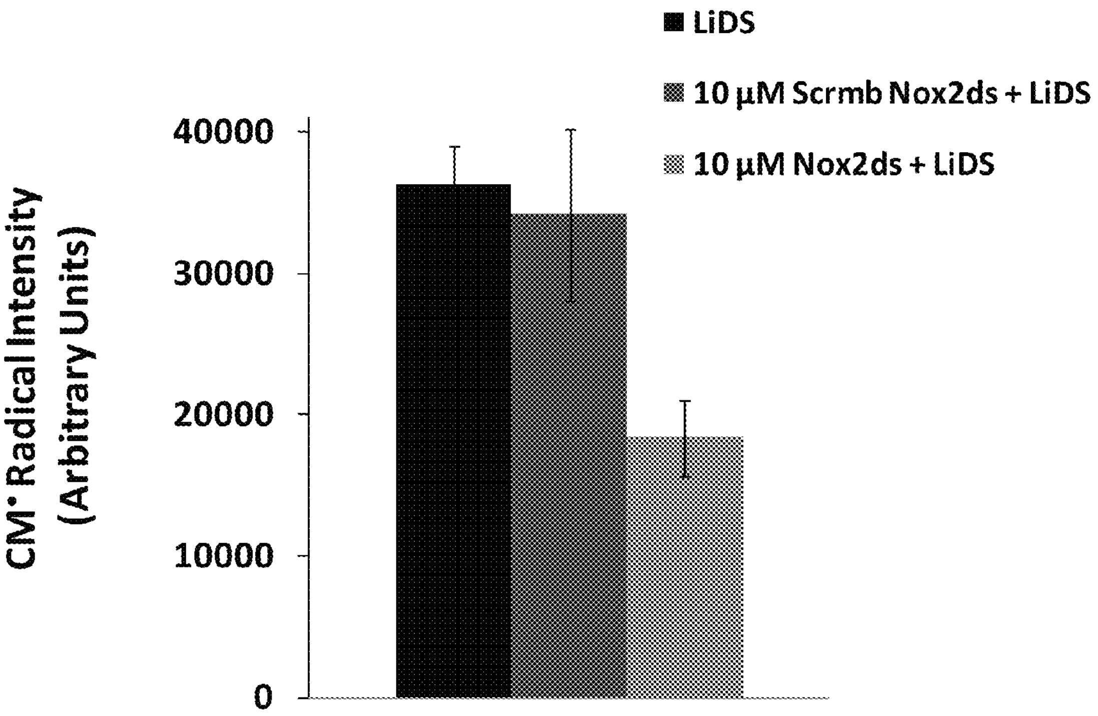
FIG. 3B is a graph showing $O_2^-$ production measured in Nox2ds or Scrmb pre-treated COS-Nox2 lysates with the EPR spin probe CMH. $O_2^-$ production was initiated by the addition of NADPH. CMH radical intensity was measured for 10 min.

FIG. 3B shows $O_2^-$ production measured in Nox2ds or Scrmb pre-treated COS-Nox2 lysates with the EPR spin probe CMH. $O_2^-$ production was initiated by the addition of NADPH. CMH radical intensity was measured for 10 min. These data confirm findings shown in FIG. 3A using another well-accepted detector of $O_2^-$.

Figure 4:
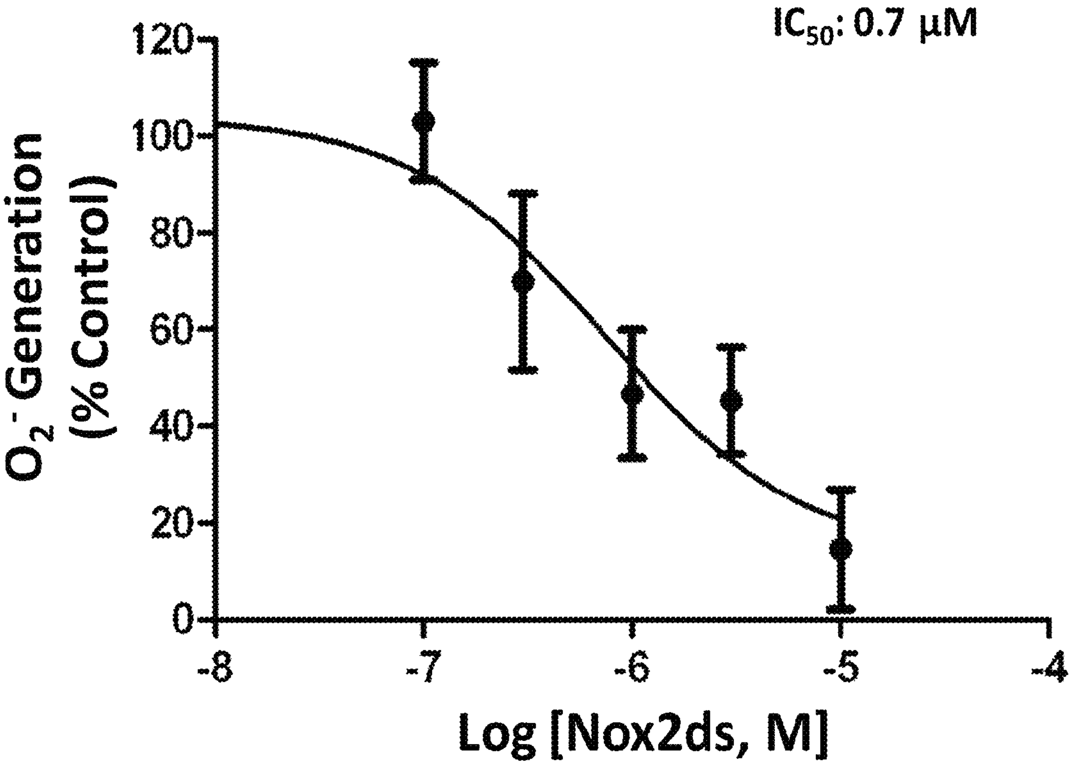
FIG. 4 is a graph showing the determination of 50% inhibitory concentration ($IC_{50}$) of Nox2ds against $O_2^-$ production in COS-Nox2 lysate.

FIG. 4 shows the determination of 50% inhibitory concentration ($IC_{50}$) of Nox2ds against $O_2^-$ production in COS-Nox2 lysate. These data demonstrate the high degree of efficacy and potency of Nox2ds.

Figure 5:
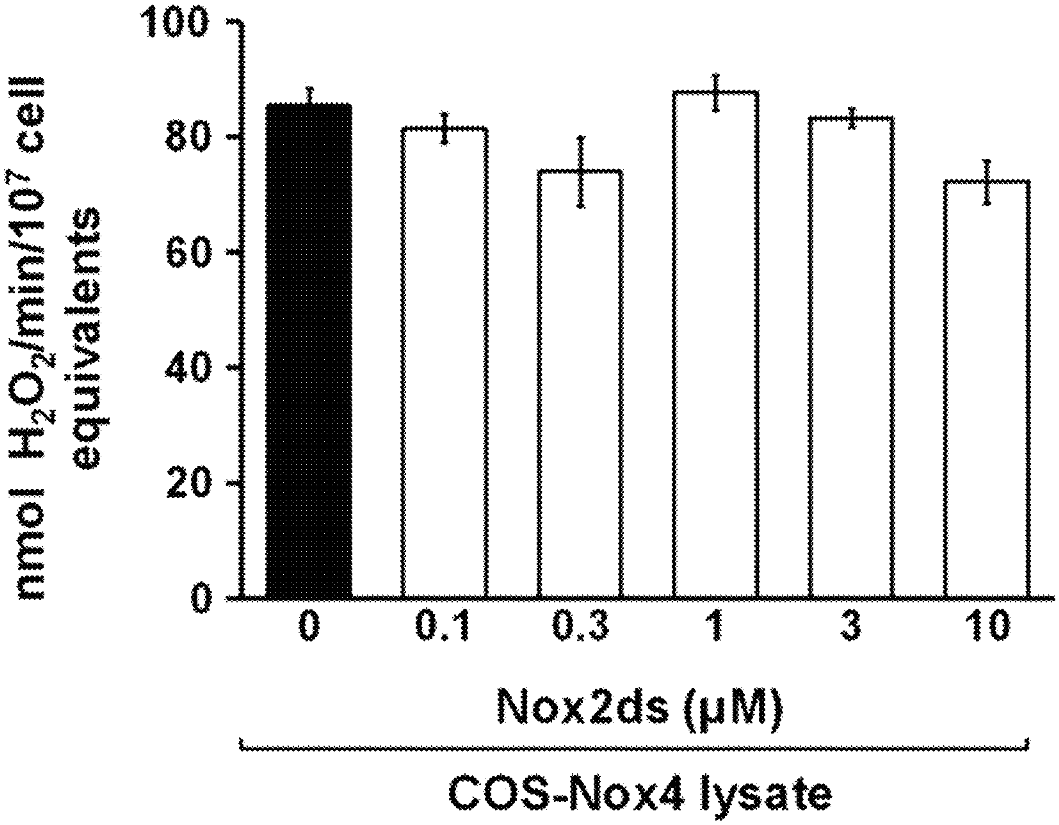
FIG. 5 is a graph showing the rate of $H_2O_2$ production in COS-Nox4 lysates pretreated with Nox2ds. $H_2O_2$ production was initiated by the addition of NADPH and measured by Amplex Red for 10 min.

FIG. 5 shows that Nox2ds does not inhibit $H_2O_2$ production in COS-Nox4 cell lysates. FIG. 5 shows the rate of $H_2O_2$ production in COS-Nox4 lysates pretreated with Nox2ds. $H_2O_2$ production was initiated by the addition of NADPH and measured by Amplex Red for 10 min. These data support specificity of Nox2ds by not inhibiting Nox4.

Figure 6:
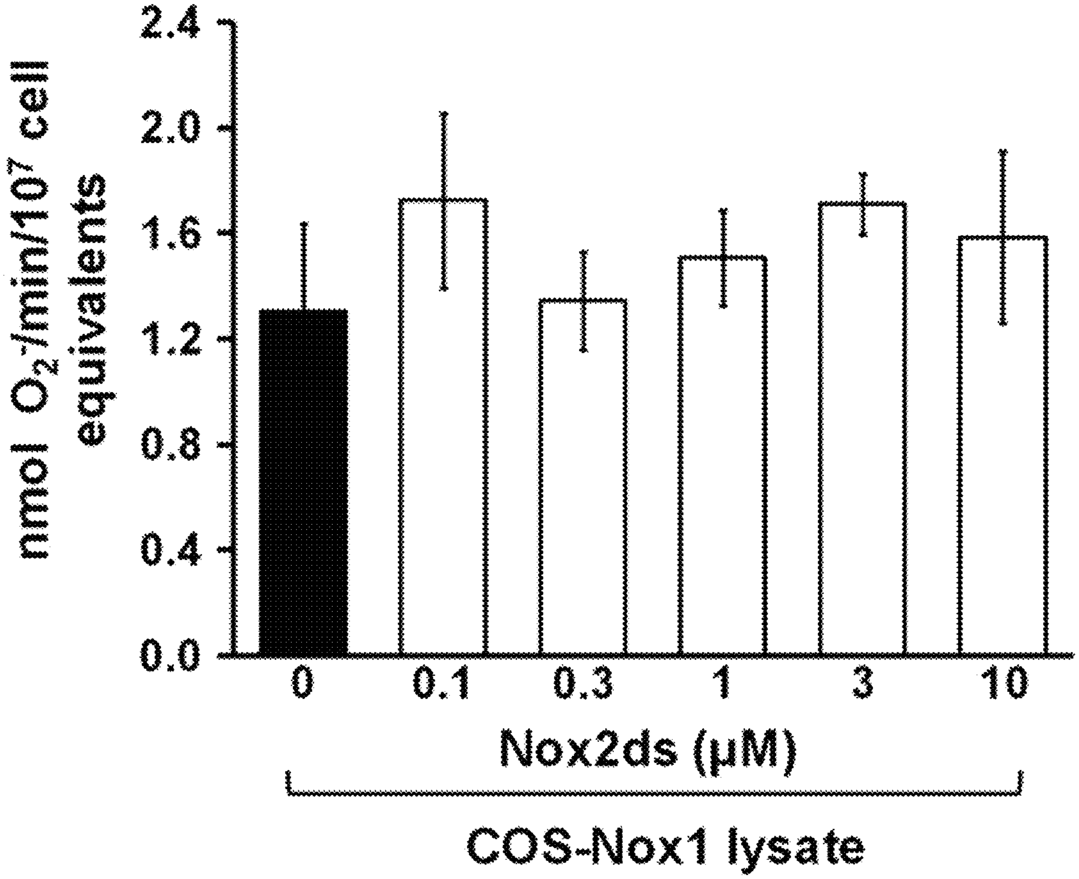
FIG. 6 is a graph showing the rate of $O_2^-$ production in COS-Nox1 lysates pretreated with Nox2ds. $O_2^-$ production was initiated by the addition of NADPH and measured by the SOD-inhibitable cytochrome c reduction for 10 min.

FIG. 6 shows the rate of $O_2^-$ production in COS-Nox1 lysates pretreated with Nox2ds. $O_2^-$ production was initiated by the addition of NADPH and measured by the SOD-inhibitable cytochrome c reduction for 10 min. FIG. 6 shows that Nox2ds Does Not Inhibit $O_2^-$ Production in COS-Nox1 Cell Lysates. These data support specificity of Nox2ds by not inhibiting Nox1.

Example 2

Aerosolized Nox2ds Attenuates Right Ventricular Hypertrophy in Hypoxia-Induced Pulmonary Hypertension in Mice Nebulization was performed using a peptide solution of 5.6 mg of the Nox2ds-tat polypeptide—RKKRRQRRRC-STRIRRQL (SEQ ID NO: 7)—was dissolved in 5 mL of PBS. The polypeptide-containing solution was placed in a nebulization chamber which consisted of a Plexiglas living environment measuring 24×10×9 in. A diffuser was placed in front of the inlet to allow equal distribution of nebulized droplets, and a controlled fan pulled air through the environment The polypeptide was delivered to mice (C57BL/6, n=2) at an air flow rate of 8 L/minute for 20 minutes per treatment. Treatment was repeated every other day for 21 days.

Figure 7:
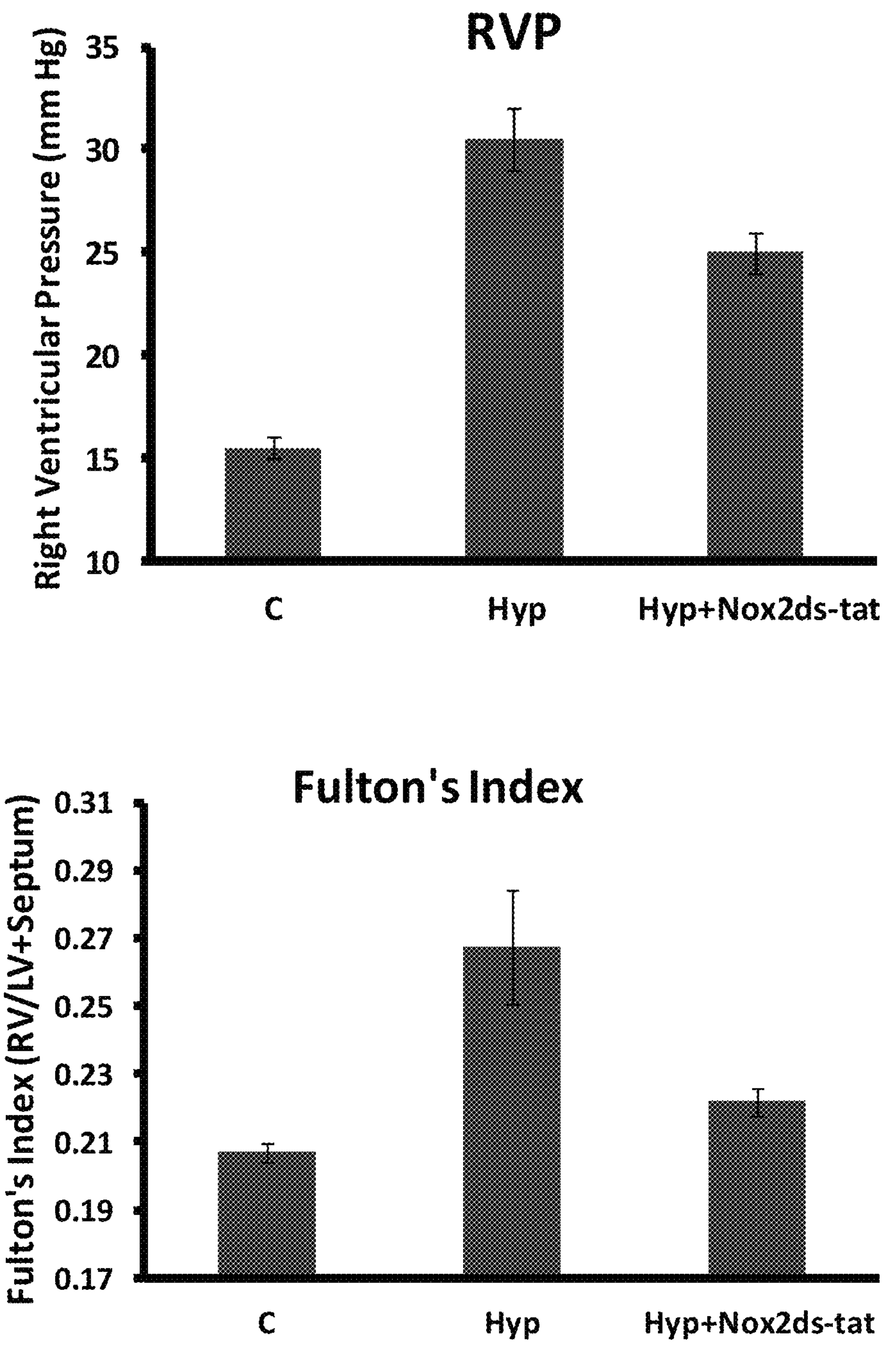
FIG. 7 shows the effect of aerosolized Nox2ds-tat on the development of right ventricular hypertrophy in hypoxia-induced pulmonary hypertension.

FIG. 7 shows the effect of aerosolized Nox2ds-tat on the development of right ventricular hypertrophy in hypoxia-induced pulmonary hypertension. FIG. 7 (top panel) is a graph showing right ventricular pressure and FIG. 7 (bottom panel) is a graph showing the Fulton's Index for the mice tested. To obtain a Fulton's Index, the heart and lungs are excised and weighed, and the ratio of RV free wall weight over septum plus left ventricular (LV) free wall weight is estimated and used as the index of RV hypertrophy.

Invasive hemodynamics to examine RV function were carried out using pressure-volume loop analysis (Scisence P/V loop hardware, London, Ontario with IOX2 analysis software, EMKA, Falls Church, Va.). Contractility index (dP/dtmax/IP), Powermax/EDV, and ejection fraction as indicators of RV systolic function as well as the time constant of relaxation (Tau) and dP/dtmin as measures of RV relaxation were determined.

From the data presented above, the following conclusions may be made:

Nox2ds concentration-dependently inhibited $O_2^-$ production in COS-Nox2 lysate, whereas its scrambled control did not.

Nox2ds is a potent and efficacious inhibitor of Nox2 NADPH oxidase with an $IC_{50}$ of 0.7 μM.

Nox2ds pre-incubation did not inhibit either COS-Nox4 lysate $H_20_2$ production or COS-Nox1 lysate $O_2^-$ production.

Aerosolized Nox2ds peptide attenuated right ventricular hypertrophy and RV pressure in hypoxia-induced pulmonary hypertension in mice.

The data demonstrates selectivity of Nox2ds peptide in differentiating the contribution of Nox2- vs. Nox1- and Nox4-NADPH oxidase and illustrates its potential for clinical use in patients with cardiopulmonary diseases.

Whereas particular embodiments of this invention have been described above for purposes of illustration, it will be evident to those skilled in the art that numerous variations of the details of the present invention may be made without departing from the invention as defined in the appended claims.

I claim:

1. A method of treating a condition of the heart, lungs, or blood vessels connecting the heart and the lungs mediated by Nox2 in a patient, comprising decreasing superoxide anion production by Nox2 in an amount and duration effective to relieve one or more symptoms of the condition in the patient by administering to the patient by inhalation an aerosolized polypeptide consisting of: a) a 9-12 amino acid fragment comprising the amino acid sequence CSTRVRRQL (SEQ ID NO: 4) and b) a tat cell penetration peptide, wherein the tat cell penetration peptide is conjugated to the amino acid fragment, and wherein the condition is one or more of right ventricular hypertrophy, pulmonary hypertension, acute lung injury, obstructive sleep apnea, ischemia/reperfusion injury in the lung, and pulmonary fibrosis.

2. The method of claim 1, wherein the polypeptide consists of RKKRRQRRRCSTRVRRQL (SEQ ID NO: 5).

3. The method of claim 1, wherein the condition is right ventricular hypertrophy.

4. The method of claim 1, wherein the condition is pulmonary hypertension.

5. The method of claim 1, wherein the condition is acute lung injury.

6. The method of claim 1, wherein the condition is pulmonary fibrosis.

7. The method of claim 1, wherein the condition is obstructive sleep apnea.

8. The method of claim 1, wherein the condition is ischemia/reperfusion injury in the lung.

9. The method of claim 1, wherein the tat cell penetration peptide consists of RKKRRQRRR (SEQ ID NO: 13).

10. The method of claim 1, wherein the fragment a) consists of CSTRVRRQL (SEQ ID NO: 4).

11. A method of treating a condition of the heart, lungs, or blood vessels connecting the heart and the lungs mediated by Nox2 in a patient, comprising decreasing superoxide anion production by Nox2 in an amount and duration effective to relieve one or more symptoms of the condition in the patient by administering to the patient by inhalation an aerosolized polypeptide consisting of: a) an amino acid fragment consisting of the amino acid sequence CSTRVRRQL (SEQ ID NO: 4) and b) a cell penetration peptide sequence, wherein the cell penetration peptide sequence is conjugated to the amino acid fragment, and wherein the condition is one or more of right ventricular hypertrophy, pulmonary hypertension, acute lung injury, obstructive sleep apnea, ischemia/reperfusion injury in the lung, and pulmonary fibrosis.

12. The method of claim 11, wherein the polypeptide consists of RKKRRQRRRCSTRVRRQL (SEQ ID NO: 5).

13. The method of claim 11, wherein the condition is right ventricular hypertrophy.

14. The method of claim 11, wherein the condition is pulmonary hypertension.

15. The method of claim 11, wherein the condition is acute lung injury.

16. The method of claim 11, wherein the condition is pulmonary fibrosis.

17. The method of claim 11, wherein the condition is obstructive sleep apnea.

18. The method of claim 11, wherein the condition is ischemia/reperfusion injury in the lung.

19. The method of claim 11, wherein the cell penetration peptide sequence is selected from the group consisting of tat, oligoarginine, p-antp, plsl, transportan, MPG, and Pep-1.

20. The method of claim 19, wherein the tat cell penetration peptide consists of RKKRRQRRR (SEQ ID NO: 13).

* * * * *

UNITED STATES PATENT AND TRADEMARK OFFICE
CERTIFICATE OF CORRECTION

| | | |
|---|---|---|
| PATENT NO. | : 9,585,933 B2 | Page 1 of 1 |
| APPLICATION NO. | : 14/608655 | |
| DATED | : March 7, 2017 | |
| INVENTOR(S) | : Patrick J. Pagano | |

It is certified that error appears in the above-identified patent and that said Letters Patent is hereby corrected as shown below:

On the Title Page

Item (73), Column 1, Line 1, delete "Pennsylvania" and insert -- Pittsburgh --

Signed and Sealed this
Fourth Day of July, 2017

Joseph Matal
*Performing the Functions and Duties of the*
*Under Secretary of Commerce for Intellectual Property and*
*Director of the United States Patent and Trademark Office*